United States Patent
Porubek et al.

(10) Patent No.: US 6,780,865 B1
(45) Date of Patent: Aug. 24, 2004

(54) COMPOUNDS HAVING SELECTIVE HYDROLYTIC POTENTIALS

(75) Inventors: David Porubek, Seattle, WA (US); Anil M. Kumar, Seattle, WA (US); Charles R. Bredl, Kent, WA (US); J. Peter Klein, Vashon, WA (US)

(73) Assignee: Cell Therapeutics, Inc., Seattle, WA (US)

( * ) Notice: Subject to any disclaimer, the term of this patent is extended or adjusted under 35 U.S.C. 154(b) by 1371 days.

(21) Appl. No.: 08/932,834

(22) Filed: Sep. 18, 1997

Related U.S. Application Data

(63) Continuation of application No. 08/328,632, filed on Oct. 25, 1994, now abandoned, which is a continuation-in-part of application No. 08/306,091, filed on Sep. 14, 1994, now abandoned, which is a continuation-in-part of application No. 08/199,368, filed on Feb. 18, 1994, now abandoned.

(51) Int. Cl.[7] .................... C07D 473/10; A61K 31/522
(52) U.S. Cl. .............. 514/263.2; 514/263.36; 514/263.21; 514/263.22; 514/263.35; 544/267; 544/269; 544/271
(58) Field of Search ................. 544/268, 267, 544/269, 271; 514/263, 263.2, 263.21, 263.22, 263.35, 263.36

(56) References Cited

FOREIGN PATENT DOCUMENTS

| EP | 286041 | * 10/1988 |
| EP | 17684 | * 9/1993 |

OTHER PUBLICATIONS

Allevi et al., *Tetrahedron Letters*, vol. 33, No. 33, pp. 4831–4834, "A Short and Simple Synthesis of the Antitumor Agent Etoposide", 1992.
Bundgaard, et al., *J. Med. Chem.*, vol. 32, No. 12, pp. 2503–2507, "A Novel Solution–Stable, Water–Soluble Prodrug Type for Drugs Containing a Hydroxyl or an NH–Acidic Group", 1989.
Hussain et al., *J. Pharma. Sci.*, vol. 76, No. 5, pp. 356–358, "Improvement of the Oral Bioavailability of Naltrexone in Dogs: A Prodrug Approach", 1987.
Riley et al., *J. Chem. Education*, vol. 65, No. 11, pp. 947–953, "The Prodrug Concept and New Drug Design and Development", 1988.

* cited by examiner

Primary Examiner—Mark L. Berch
(74) Attorney, Agent, or Firm—Foley & Lardner, LLP

(57) ABSTRACT

Disclosed are compounds having selective hydrolytic potential. The disclosed compounds are useful as compounds having selective stability and are capable of undergoing programmed hydrolysis in biologic systems. The disclosed compounds have a structure of formula I:

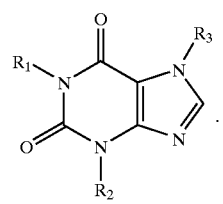

21 Claims, 10 Drawing Sheets lisofylline      inventive compound

COMPOUNDS HAVING SELECTIVE HYDROLYTIC POTENTIALS

CROSS-REFERENCE TO RELATED APPLICATION

This application is a continuation of application Ser. No. 08/328,632, filed Oct. 25, 1994, now abandoned, which is a Continuation-In-Part of application Ser. No. 08/306,091 filed on Sep. 14, 1994, now abandoned, which is a Continuation-In-Part of application Ser. No. 08/199,368 filed on Feb. 18, 1994, now abandoned.

TECHNICAL FIELD OF THE INVENTION

The invention provides compounds having selective (programmed) stability in adverse chemical and dynamic biologic environments. The disclosed compounds permit selective control of the extent and rate of conversion of the inventive compounds to a hydroxyl-substituted chiral xanthine compound.

BACKGROUND OF THE INVENTION

Drugs possessing a chiral center generally are developed, tested, manufactured and marketed as racemates, containing equivalent amounts of each respective enantiomer. In biologic systems, one enantiomer may be an active compound while the other enantiomer may have little or no effect. Therefore in some instances, skilled artisans may seek to enhance efficacy, improve potency or prolong therapeutic potential by isolating efficacious enantiomers from nonactive ones.

Enantiomerically pure compounds have been prepared by first synthesizing a racemate, and then, using chiral separation techniques, isolating the enantiomers. Manufacturing and dosing drugs as racemic mixtures means that each drug dose contains an equivalent amount of a corresponding isomer, sometimes having little or no therapeutic potential and quite possibly may cause unsuspected and undesirable side affects.

Thus, in many biologic systems, to attain, inter alia, greater potency or prolonged efficacy of compounds in the laboratory, a need exists to administer substantially pure enantiomers for use as pharmaceuticals. An example of one such pure enantiomer is the compound lisofylline, 1-(5-(R)-hydroxyhexyl)-3,7-dimethylxanthine, (described in U.S. application Ser. No. 08/307,554 filed on Sep. 16, 1994 (now pending), the entire disclosure of which is incorporated by reference herein). Lisofylline is useful for a wide variety of therapeutic indications, including, for example, treating sepsis and sepsis syndrome, preventing multi-organ dysfunction associated with trauma, increasing the production of multi-lineage hematopoietic cells after cytoreductive therapies, promoting trilineage engraftment after bone marrow transplantation, and alleviating the toxic side effect of interleukin-2 (IL-2), amphotericin B, cyclosporin A, FK506 or granulocyte macrophage colony stimulating factor (GM-CSF) therapies.

In vitro and in vivo studies and human clinical trials with i.v. administered lisofylline confirm therapeutic efficacy of this substantially pure enantiomer. Further studies in predictive animal models (e.g., mouse, rat and dog models) using lisofylline as an oral formulation conclusively indicate that the chiral lisofylline is absorbed as a chiral molecule. Oral administration of a drug is often desired for, inter alia, ease of use, self-administered therapy and cost reduction; and thus, an orally administered drug, which eliminates more invasive i.v. and i.p. procedures is desirable.

In general, therapeutic deficiencies of new or existing drugs usually result from difficulties in any of three phases of drug action: pharmaceutic, biopharmaceutic, and pharmacodynamic. The pharmaceutic phase refers to the chemical and physical environment of a drug prior to its absorption into the living system and includes the dosage form of the drug as well as tissues encountered at the site of administration. The biopharmaceutic phase of drug action include absorption, distribution, biotransformation, and elimination of the drug. The pharmacodynamic phase deals with the drug at its pharmacologic site(s) of action. Difficulty associated with any of these three phases of drug action can result in either a subtherapeutic or toxic response of the patient to drug therapy. Riley, T. N., "The Concept and New Drug Design and Development," *Journal of Chemical Education*, Vol. 65 No. 11, pages 947–953, November 1988.

In orally administered, enantiomerically pure pharmaceuticals, a compound must retain its efficacious properties and chemical and chiral structure throughout various degrative biologic systems enroute to the bloodstream after ingestion. Such systems, which are encountered enroute to merging with systemic blood flow include, for example, digestion (stomach gastric juices), metabolism (intestinal membrane, portal vein and liver blood) and blood filtration (kidney and especially liver). Skilled artisans strive to minimize a first pass effect. The first pass effect is defined as those processes, such as digestion, metabolism and blood filtration which alter the drug such that it becomes inactive. An objective in minimizing the first pass effect is to increase bioavailability of orally administered pharmaceutical compounds. An increased systemic concentration of a therapeutic compound for a longer period of time corresponds to higher bioavailability.

A prodrug is defined as a pharmacologic precursor (parent) to an active compound, which itself alone may possess efficacious properties. Conversion of a prodrug to an active compound occurs by either chemical or enzymatic processes after administration. Riley, supra. Altering the chemical structure of a compound may include modification of structural features requiring sophisticated chemical or biochemical mechanisms to generate the parent specie.

The preparation of a "prodrug" form of another compound can have a number of beneficial effects in terms of increasing therapeutic utility of the therapeutic compound. Such beneficial effects include, for example, improved chemical stability characteristics, improved absorption characteristics following oral administration, better taste to improve patient compliance upon oral administration, and improved pharmacodynamics and pharmacokinetic characteristics, including altering metabolism of the parent chiral drug.

Target compounds as prodrug candidates must be stable in a variety of chemical and biologic systems, including the gastrointestinal tract and whole blood so as to have maximum effect on increasing bioavailability of an intended -pharmaceutical in vivo. Yet, these candidates need not liberate a parent compound quickly or completely prior to or during ingestion or in the liver to achieve this result, and often it is undesirable to do so.

Because of the complexity of some biologic systems and the specificity of compounds as they relate to particular chemical or enzymatic pathways, success of one prodrug approach is not conclusive of proof of success for other drugs having differing structures and targeted therapeutic potential. Problems with solubility, toxicity, stability, bioavailability all vary between drugs. Bundgaard et al., "A Novel Solution-Stable, Water-Soluble Prodrug Type for Drugs Containing a Hydroxyl or an NH-Acidic Group," *Journal of Medicinal Chemistry*, Vol. 32, No. 12, pages 2503–2507, December 1989.

Hussain et al. disclose selected prodrugs of Naltrexone, used in treating opioid addiction. "Improvement of the Oral Bioavailability of Naltrexone in Dogs: A Prodrug Approach," *Journal or Pharmaceutical Sciences*, Vol. 76, No. 5, pages 356–358, May 1987. The disclosed prodrugs include anthranilate, acetylsalicylate, benzoate and pivalate esters of Naltrexone. Naltrexone has numerous chiral centers, but Hussain et al. were concerned only with bioavailability of the racemic compound. Of the four esters disclosed, only the anthranilate and acetylsalicylate esters exhibited substantially higher bioavailability when compared with the bioavailability for orally administered Naltrexone. But, as acknowledged by Hussain et al., there is no correlation between bioavailability and the in vitro hydrolysis half-life. Thus, identifying and isolating a prodrug having the necessary characteristics to minimize or eliminate the first pass effect is a difficult task. In particular, lisofylline, its efficacious properties primarily a result of its specific enantiomeric stereochemistry, made a search for a corresponding oral prodrug of lisofylline very difficult.

The invention is in response to an identified need to develop compounds that have selective stability in adverse chemical and metabolic systems. Such compounds would ideally be capable of maintaining enantiomeric stereochemistry, but when exposed to an adverse chemical or biologic environment (whether in vitro or in vivo), would maintain their chemical properties, having their own efficacious properties, or could be converted to a corresponding therapeutic compound. The invention results from these efforts to discover compounds, heretofore unknown, which structurally would have not only specific, variable abilities to maintain enantiomeric chemistry, but also programmed stability in dynamic, metabolic systems.

SUMMARY OF THE INVENTION

The inventive compounds possess varying stabilities and different rates of hydrolysis to a corresponding alcohol. Such differences correlate to programmed hydrolytic potential. These differences are characteristic of varying chemical structures and thus programmed rates of hydrolysis are compound specific. More particularly, the invention provides a compound comprising a xanthine core of the formula I or a pharmaceutically acceptable salt, solvate or hydrate thereof:

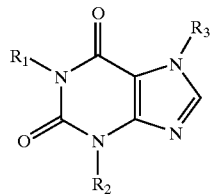

I

One of $R_1$ or $R_2$ is independently an aliphatic hydrocarbon having the formula II:

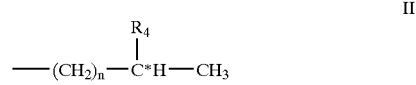

II

In formula II, n is an integer from about four to about eight, $R_1$ or $R_2$, which is other than formula II, and $R_3$ are independently $C_{(1-12)}$ alkyl and $C^*$ is a chiral carbon atom. $R_4$ is an amino acid or carbohydrate attached to the chiral carbon atom $C^*$ via an ester linkage, or $-O-X-(R_5)_m$.

If $R_4$ is $-O-X-(R_5)_m$, m is two or three, X is selected from the group consisting of C, P or S and $R_5$ is a hydrogen atom; hydroxyl group; =O; substituted or unsubstituted $C_{(1-10)}$ alkyl, $C_{(1-10)}$ alkenyl, $C_{(1-10)}$ alkynyl, $C_{(1-10)}$ alkoxyl, $C_{(1-10)}$ oxoalkyl, or $C_{(1-10)}$ acetoxyl, $C_{(1-10)}$ carboxyalkyl, or $C_{(1-10)}$ hydroxyalkyl group; $-OR_6$, $R_6$ being a substituted or unsubstituted $C_{(1-10)}$ alkyl, $C_{(1-10)}$ alkenyl, $C_{(1-10)}$ alkynyl; $C_{(1-10)}$ oxoalkyl; substituted or unsubstituted cyclic or heterocylic group having from one- to three-rings, each ring containing from four to seven atoms.

These chiral inventive compounds provide for selectively stable compounds, both in vitro and in vivo. In more preferred compounds of the invention, a specific moiety chirally linked to the lisofylline skeleton permits control of the extent and rate of conversion of the inventive compounds to a corresponding alcohol. An acidic or basic environment, or when administered orally, various intestinal enzymes, or plasma or liver enzymes, hydrolyze the inventive compounds to form a corresponding alcohol. Thus, the present invention provides, inter alia, prodrugs for active chiral secondary ω-1 hydroxyl-substituted xanthine compounds.

DETAILED DESCRIPTION OF PREFERRED EMBODIMENTS

Figure 1:
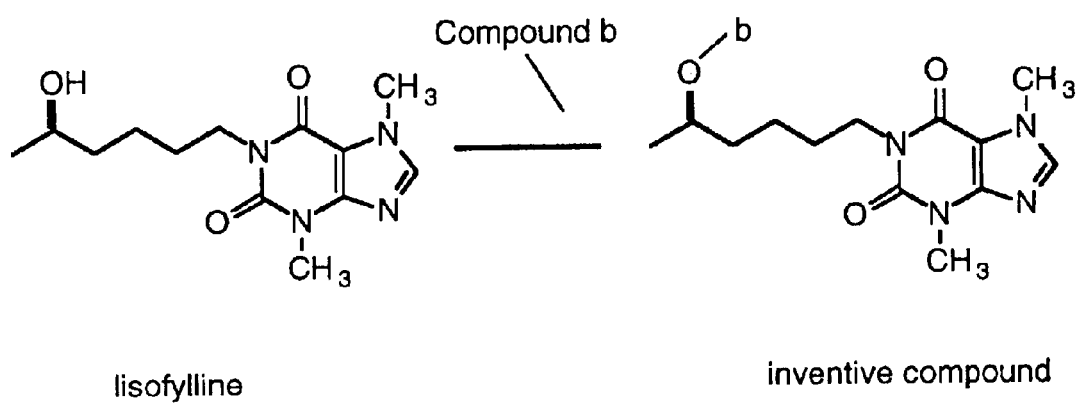
FIG. 1 is a schematic representation of a general synthesis of an inventive compound from lisofylline.

The inventive compounds include, inter alia, compounds that form the hydoxyl-substituted xanthine, lisofylline in vivo. Of the various advantages of the compounds, these compounds have a primary, characteristic benefit: selective enantiomeric stability coupled with varying resistance to hydrolysis. Having performed detailed studies of lisofylline, its in vivo, metabolic pathway and corresponding affect on its therapeutic potential, a class of novel compounds was discovered having structures and chemical properties that were previously unknown.

Compounds and Compositions

The present invention provides a chiral to- I hydroxyl substituted xanthine compound comprising a xanthine core of formula I:

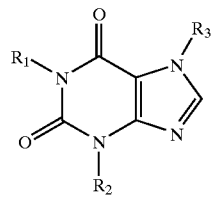

One of $R_1$ or $R_2$ is independently an aliphatic hydrocarbon having the formula II:

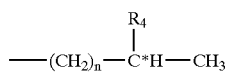

In formula II, n is an integer from about four to about eight, $R_1$ or $R_2$, which is other than formula II, and $R_3$ are independently $C_{(1-12)}$ alkyl and C* is a chiral carbon atom. $R_4$ is an amino acid or carbohydrate attached to the chiral carbon atom C* via an ester linkage, or —O—X—$(R_5)_m$.

If $R_4$ is —O—X—$(R_5)_m$, m is two or three, X is selected from the group consisting of C, P or S and $R_5$ is a hydrogen atom; hydroxyl group; =O; substituted or unsubstituted $C_{(1-10)}$ alkyl, $C_{(1-10)}$ alkenyl, $C_{(1-10)}$ alkynyl, $C_{(1-10)}$ alkoxyl, $C_{(1-10)}$ oxoalkyl, or $C_{(1-10)}$ acetoxyl, $C_{(1-10)}$ carboxyalkyl, or $C_{(1-10)}$ hydroxyalkyl group; —$OR_6$, $R_6$ being a substituted or unsubstituted $C_{(1-10)}$ alkyl, $C_{(1-10)}$ alkenyl, $C_{(1-10)}$ alkynyl; $C_{(1-10)}$ oxoalkyl; substituted or unsubstituted cyclic or heterocyclic group having from one- to three-rings, each ring containing from four to seven atoms.

Representative amino acids may be naturally occurring or synthesized. Examples of amino acids include, without limitation, alaninyl, argininyl, asparaginyl, aspartyl, cysteinyl, glutaminyl, glutamyl, glycinyl, histidinyl, isoleucinyl, leucinyl, lysinyl, methioninyl, phenylalaninyl, prolinyl, serinyl, threoninyl, tryptophanyl, tyrosinyl, valinyl. Representative, non-limiting carbohydrates include glucosyl, glucosidyl, maltosyl, glucopyranosidyl, glyceraldehydyl, erythrosyl, arabinosyl, ribolucosyl, fructosyl, erythrtolyl, xylosyl, lyxosyl, allosyl, altrosyl, mannosyl, mannosidyl, gulosyl, idosyl, galactosyl or talosyl.

If $R_4$ is —O—X—$(R_5)_m$, m is two or three, X is selected from the group consisting of C, P or S and $R_5$ is a hydrogen atom; hydroxyl group; =O; substituted or unsubstituted $C_{(1-10)}$ alkyl, $C_{(1-10)}$ alkenyl, $C_{(1-10)}$ alkynyl, $C_{(1-10)}$ alkoxyl, $C_{(1-10)}$ oxoalkyl, or $C_{(1-10)}$ acetoxyl or $C_{(1-10)}$ hydroxyalkyl group; —$OR_6$, $R_6$ being a substituted or unsubstituted $C_{(1-10)}$ alkyl, $C_{(1-10)}$ alkenyl, $C_{(1-10)}$ alkynyl or $C_{(1-10)}$ oxoalkyl; substituted or unsubstituted cyclic or heterocyclic group having from one- to three-rings, each ring containing from four to seven atoms.

In preferred inventive compounds, X is C. If $R_4$ is —O—X—$(R_5)_m$, more preferred compounds have at least one $R_5$ that is =O and m is two.

Representative, non-limiting examples of substituents for the substituted $C_{(1-10)}$ alkyl, $C_{(1-10)}$ alkenyl, $C_{(1-10)}$ alkynyl, $C_{(1-10)}$ alkoxyl, $C_{(1-10)}$ oxoalkyl, or $C_{(1-10)}$ acetoxyl, cyclic or heterocylic groups include: amido, amino, $C_{(1-6)}$ alkenyl, $C_{(1-6)}$ alkyl, $C_{(1-6)}$ alkoxyl, primary, secondary or tertiary $C_{(1-6)}$ hydroxyalkyl, $C_{(1-6)}$ oxoalkyl, azido, carbonyl, carboxylic acid, cyano, $C_{(1-6)}$ haloalkyl, isocyano, isothiocyano, phosphatyl, phosphonatyl, sulfonatyl, sulfonyl, sulfoxyl, imino, thioamido, thiocarbonyl, thioalkoxyl, thioloxoalkyl and thio groups or a single atom. The single atom may be oxygen, chlorine, bromine or fluorine. The $C_{(1-6)}$ haloalkyl may be a mono, di- or tri-haloalkyl and the $C_{(1-6)}$ alkoxyl may preferably be a methoxy or ethoxy group.

Most preferred compounds of the invention have the $R_1$ or $R_2$, other than formula II, containing one or two, nonadjacent oxygen atoms, each oxygen atom replacing a single carbon atom of the $C_{(1-12)}$ alkyl.

Preferred cyclic or heterocyclic groups of the inventive compounds may include, but are not limited to, a benzyl, phenyl, biphenyl, cyclohexyl, cyclohexenyl, cyclopentyl, cyclopentenyl, cyclopentanedionyl, napthlalenyl, phenolyl, quinonyl, cyclopropyl, cyclobutyl, cycloheptyl, cycloheptenyl, indanyl, indenyl, decalinyl, resorcinolyl, tetralinyl, α-tetralonyl, 1-indanonyl, cyclohexanedionyl, cyclopentanedionyl, dimethylxanthinyl, methylxanthinyl, phthalimidyl, homophthalimidyl, methylbenzoyleneureayl, quinazolinonyl, octylcarboxamidobenzenyl, methylbenzamidyl, methyldioxotetrahydropteridinyl, glutarimidyl, piperidonyl, succinimidyl, dimethoxybenzenyl, methyldihydrouracilyl, methyluracilyl, methylthyminyl, piperidinyl, dihydroxybenzenyl or methylpurinyl, even more preferably, methylxanthinyl or dimethylxanthinyl group.

In most preferred compounds of the invention, n is 4, m is 2, and $R_2$ and $R_3$ are methyl and at least one $R_5$ is =O. The other $R_5$, other than =O, preferably may be selected from the group consisting of trimethoxy-substituted phenyl, phenolyl or benzamino. Most preferred of the amino acid, $R_4$, have $R_4$ selected from among glycinyl, isoleucinyl and valinyl.

Pharmaceutical Formulations

A suitable pharmaceutical formulation will depend on the nature of the disorder to be treated, the nature of the medicament chosen, and the judgment of the attending physician. In general, the compounds are formulated for oral administration. Suitable formulations for these compounds can be found, for example, in *Remington's Pharmaceutical Sciences* (latest edition), Mack Publishing Company, Easton, Pa.

The compounds, their pharmaceutically acceptable salts, solvates and hydrates can be employed in a wide variety of pharmaceutical forms. The preparation of a pharmaceutically acceptable salt will be determined by the chemical nature of the compound itself, and can be prepared by conventional techniques readily available. Thus, if a solid carrier is used, the preparation can be tableted, placed in a hard gelatin capsule in powder or pellet form or in the form of a troche or lozenge. The amount of solid carrier will vary widely but preferably will be from about 25 mg to about 1 gram, wherein the amount of inventive compound per dose will vary from about 25 mg to about 1 gram for an adult. When a liquid carrier is used, the preparation will be in the form of a syrup, emulsion, soft gelatin capsule, sterile injectable liquid such as an ampule or nonaqueous liquid suspension. Where the inventive composition is in the form of a capsule, any routine encapsulation is suitable, for example, using the aforementioned carriers in a hard gelatin capsule shell. Where the composition is in the form of a soft gelatin shell capsule, any pharmaceutical carrier routinely used for preparing dispersions of suspensions may be considered, for example, aqueous gums, celluloses, silicates or oils and are incorporated in a soft gelatin capsule shell. A syrup formulation will generally consist of a suspension or solution of the compound or salt thereof in a liquid carrier (e.g., ethanol, polyethylene glycol, coconut oil, glycerine or water) with a flavor or coloring agent.

The amount of inventive compound required for therapeutic effect upon administration will, of course, vary with the compound chosen, the nature and severity of the disease and the discretion of the treatment provider. The daily dosage for treatment of sepsis or another severe inflammatory condition by oral administration from about 0.001 mg/kg to about 40 mg/kg, preferably from about 0.01 mg/kg to about 20 mg/kg of an inventive compound or a pharmaceutically acceptable salt thereof, calculated as the free base.

The daily dosage regimen for oral administration is suitably from about 0.1 mg/kg to about 1000 mg/kg per day. For administration the dosage is suitably from about 0.001 mg/kg to about 40 mg/kg of the inventive compound or a pharmaceutically acceptable salt thereof, calculated as the free base. The active ingredient may be administered from 1 to 6 times a day, sufficient to exhibit activity.

While dosage values will vary, therapeutic compounds of the invention may be administered to a human subject requiring such treatment as an effective oral dose of about 50 mg to about 5000 mg per day, depending upon the weight of the patient. For any particular subject, specific dosage regimens should be adjusted to the individual's need and to the professional judgment of the person administering or supervising the administration of the inventive compounds.

Representative compounds according to the invention may include:

1515R 1-(5-Acetoxyhexyl)-3,7-dimethylxanthine

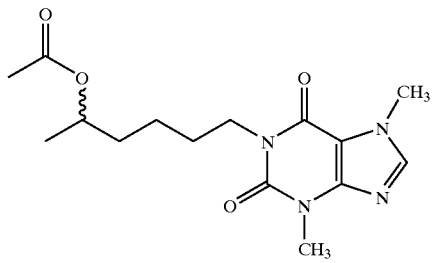

1570R 1-(5-(R)-methoxyhexyl)-3,7-dimethylxanthine

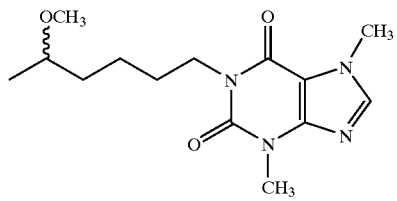

4544R R-1-(5-Pivaloyloxyhexyl)-3,7-dimethylxanthine

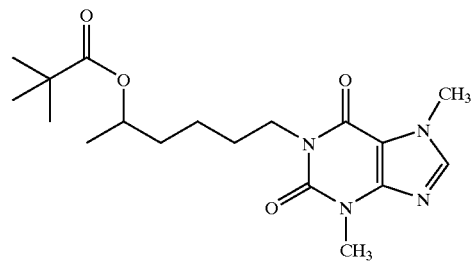

4545R R-1-(5-Benzoyloxyhexyl)-3,7-dimethylxanthine

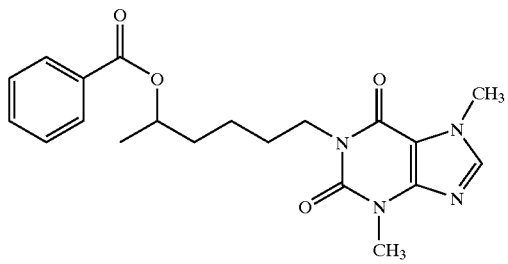

-continued
| | |
|---|---|
| 4546R R-1-(5-Methoxyacetoxyhexyl)-3,7-dimethylxanthine | 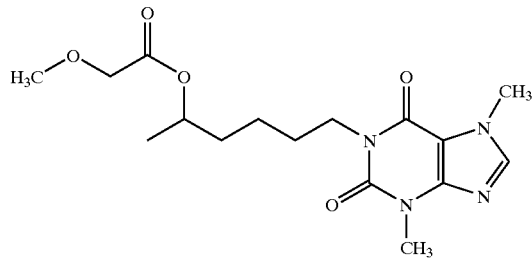 |
| 4547R R-1-(5-Pivaloyloxymethoxyhexyl)-3,7-dimethylxanthine | 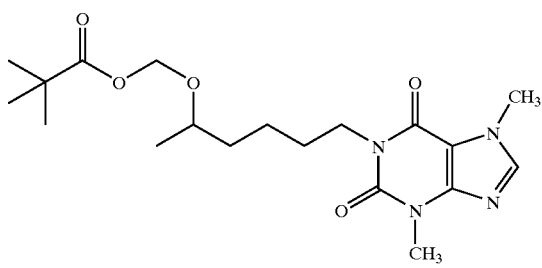 |
| 4570R R-1-(5-(3,4,5-Trimethoxybenzoyloxy)hexyl)-3,7-dimethylxanthine | 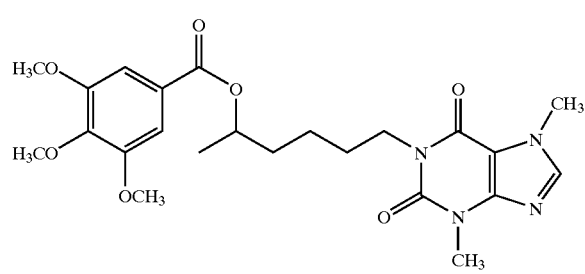 |
| 4571R R-1-(5-trans-Cinnamoyloxy)hexyl)-3,7-dimethylxanthine | 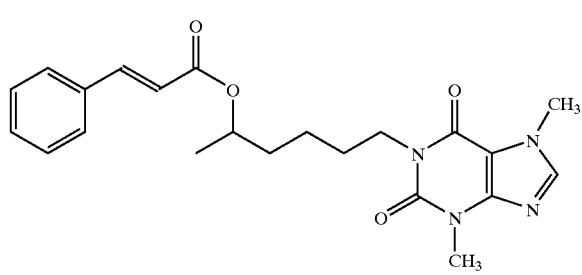 |
| 4572R R-1-(5-(Isobutyroxy)hexyl-3,7-dimethylxanthine | 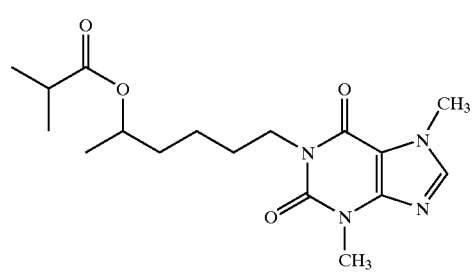 |
| 4573R R-1-(5-Butyroxy)hexyl)-3,7-dimethylxanthine | 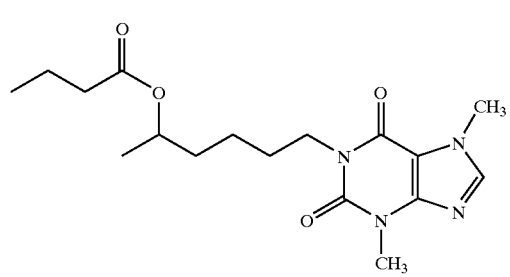 |

-continued
4574R R-1-(5-Decanoxy)hexyl)-3,7-dimethylxanthine
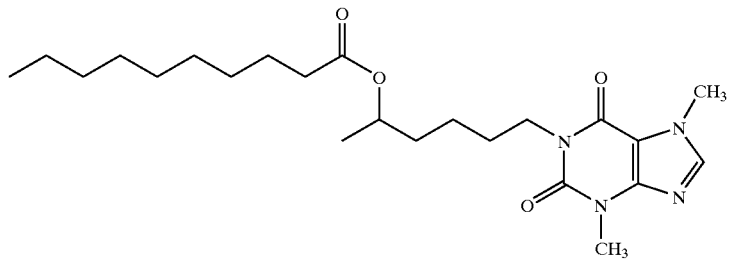
4575R R-1-(5-Propionoxy)hexyl)-3,7-dimethylxanthine
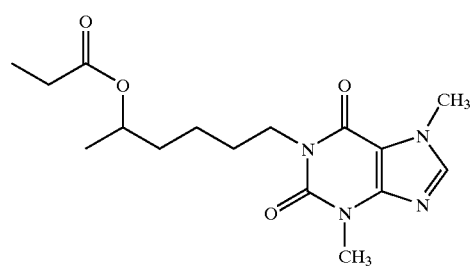
4576R R-1-(5-(3-Carboxy)propionoxy)hexyl)-3,7-dimethylxanthine
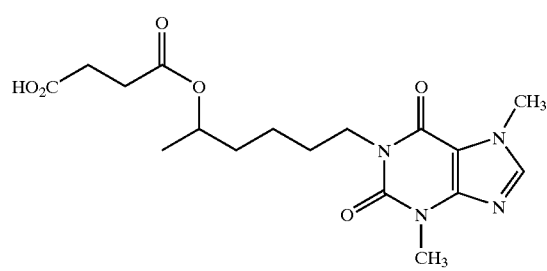
4577R R-1-(5-(Benzyloxy)hexyl)-3,7-dimethylxanthine
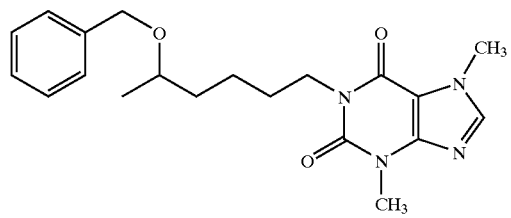
5500R R-1-(5-Hydroxy)hexyl)-3,7-dimethylxanthine glycinate ester
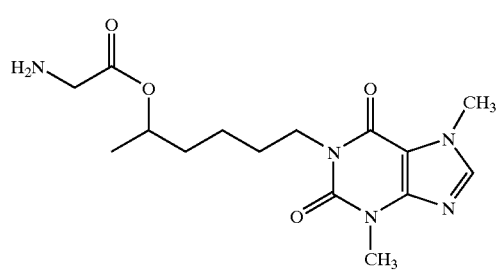
5501R R-1-(5-Hydroxy)hexyl)-3,7-dimethylxanthine isoleucinate ester
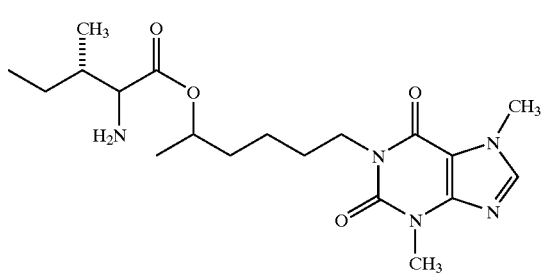

-continued
5502R R-1-(5-Hydroxy)hexyl)-3,7-dimethylxanthine valinate ester
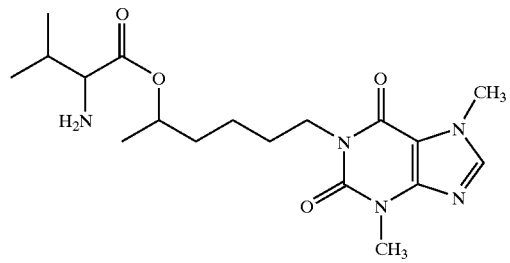
5503R R-1-(5-Hydroxy)hexyl)-3,7-dimethylxanthine phthalic acid half ester
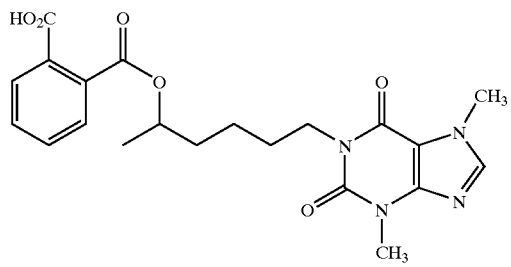
5504R R-1-(5-(4'-Hydroxybenzoyloxy)hexyl)-3,7-dimethylxanthine
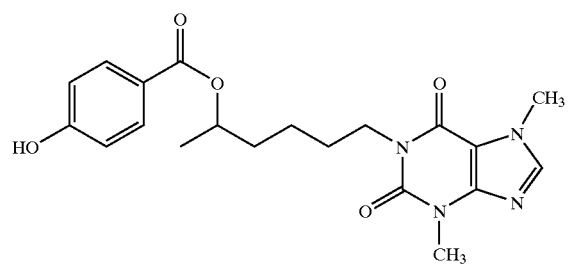
5527R R-1-(5-Hydroxy)hexyl)-3,7-dimethylxanthine anthranilate ester
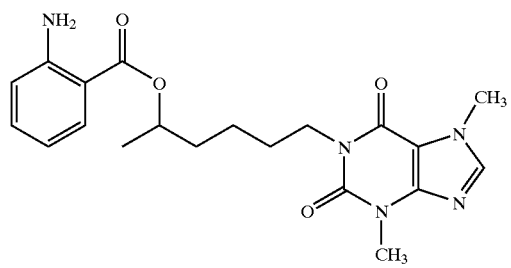
5531R R-1-(5-Hydroxy)hexyl)-3,7-dimethylxanthine N,N-dimethyl carbamate
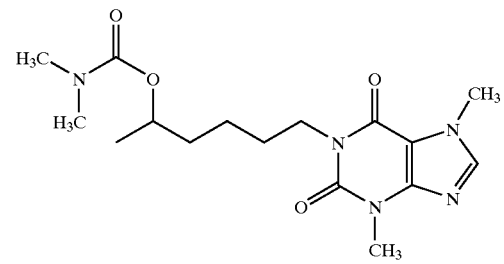

| | |
|---|---|
| 5540R R-1-(5-Hydroxy)hexyl)-3,7-dimethylxanthine nicotinate ester | 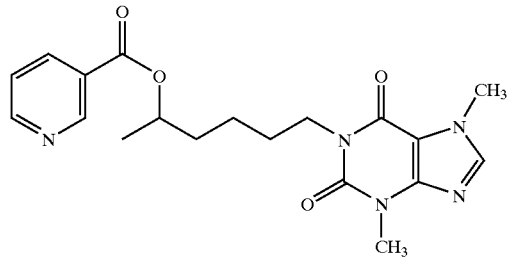 |

Although various synthetic protocols may be used by skilled artisans to prepare the inventive compounds, generally, the compounds may be prepared by reacting a starting material, lisofylline, with a compound having a structure of the functional moiety ($R_4$ of the above formula II) of these compounds. Thus, providing that starting materials are commercially available or may be readily synthesized, a variety of compounds within the scope of the invention may be synthesized by using this general method, selecting starting materials and reagents to achieve a desired product. FIG. 1 graphically represents this general synthetic process.

The following examples are illustrative of specific, preferred embodiments of the invention; however, these examples are not intended to be construed as limiting the scope of the invention as disclosed herein.

EXAMPLE 1

This example illustrates several methods of synthesizing inventive compound no. 1515R—protocols A–D, below— (see above for chemical name and structure).

A. Inventive compound no. 1515 may be prepared from lisofylline via acid catalysis. A 200 mL round bottom ("r.b.") flask was charged with lisofylline (28 g, 0.1 mol; 99% chemical purity, 93% R isomer) and acetic anhydride (51 g, 0.5 mol). The mixture was magnetically stirred and concentrated sulfuric acid (0.5 mL) was added dropwise to the stirring solution. The resulting reaction mixture was heated to reflux and maintained at reflux temperature for 16 hours. The hot mixture was drowned in ice (200 g), and the mixture neutralized and saturated with sodium bicarbonate (80 g), yielding a slurry containing a tan solid. The tan solid was taken up in ethyl acetate (500 mL) and the aqueous layer was separated and discarded.

The organic layer was washed with two, 250 mL aliquots of saturated brine, and the brine layers discarded. The organic layer was dried over sodium sulfate, filtered through a small plug of neutral alumina to remove colored impurities, and stripped to a yellow/orange thick syrup, which crystallizes on standing to an off-white solid, leaving 35.6 g of crude yield. The crude product was recrystallized from 1.5 parts ethyl acetate and 3 parts hexanes, yielding 15.4 g of colorless to off-white fluffy needles—1515R— (47.8%, 99.2% chemical purity by HPLC).

B. Inventive compound no. 1515 was also prepared from lisofylline via base catalysis. A 500 mL r.b. flask was charged with lisofylline (50 g, 0.178 mol), ethyl acetate (100 mL), triethylamine (21.6 g, 0.214 mol) and 4-dimethylaminopyridine (0.217 g, 1 mol %). The mixture was slurried and chilled to 5° C. in an ice water bath, followed by slow addition of acetic anhydride (20 g, 0.196 mol) to the mixture over 10 minutes. The slurry was allowed to warm to ambient temperature over 1 hour and was stirred at room temperature for 16 hours. The slurry became homogeneous, and TLC indicated a single spot for product. The mixture was drowned with water (150 mL) and additional ethyl acetate (100 mL). The mixture was separated and the aqueous layer was removed and discarded. The organic layer was washed with saturated brine (100 mL) and the brine layer discarded. The organic layer was dried over sodium sulfate and stripped to a yellow residue, which crystallized upon standing to yield 60.2 g of a crude off-white solid. The crude product was recrystallized from ethyl acetate/petroleum ether (30–60° C. boiling range), resulting in 29 g of colorless fluffy needles (51% yield, m.p.= 81.5–83.5, 99.8% chemical purity by HPLC).

C. Inventive compound no. 1515 was also prepared from 1-chloro-5-(R)-acetoxyhexane according to the following synthetic method. Under a slow sweep of dry nitrogen, a 250 mL, 3-neck, round-bottomed flask fitted with a reflux condenser, thermometer and pressure equalizing addition funnel was charged with sodiotheobronine (10.2 g, 50.5 mmol), and 30 mL DMSO (Gaylord high tech grade, 99.9% minimum.). The resulting slurry was stirred at ambient temperature and the vessel was charged with 1-chloro-5-(R)-acetoxyhexane (9.66 g, 50.5 mmol; 93% chemical purity). No exothermic reaction was observed.

The resulting mixture was heated to 80° C. and held at that temperature for a minimum of 6 hours. The reaction mixture cleared up over the 6 hour period to a hazy yellow solution. The mixture was drowned with water (30 mL) and cooled to ambient temperature. The mixture was drowned with isopropyl acetate (60 mL) and the mixture was stirred for 10 minutes to extract the desired product, after which the mixture was separated and the lower aqueous DMSO layer was discarded. The organic layer was washed with saturated brine (30 mL), the mixture was separated, and the brine layer discarded. The solvent of the organic layer was distilled off, leaving a thick syrup, which crystallized upon standing to obtain 14.5 g of crude product. The crude product was recrystallized from isopropyl acetate/isooctane in 76% yield and 96.5% chemical purity.

D. Inventive compound no. 1515 was also prepared from 1-bromo-5-(R)-acetoxyhexane according to the following synthetic method. The synthetic procedure described in detail in paragraph C above was repeated, except that the resulting slurry (after addition of sodiothobromine) was charged with 1-bromo-5-(R)-acetoxyhexane, instead of 1-chloro-5-(R)-acetoxyhexane. In addition, the reaction mixture was heated at 55–60 ° C. for 16–24 hours, and the reaction mixture was drowned with up to 60 mL water. The desired product was instead extracted with toluene or ethyl acetate instead of isopropyl acetate.

EXAMPLE 2

This method illustrates a method of synthesis for inventive compound no. 1507R (see above for chemical names and structure). A 250 mL two-necked flak fitted with an argon inlet and a septum was charged with (95%) sodium hydride (360 mg; 15 mmol). A solution of lisofylline (2.8 g, 10 mmol) in tetrahydrofuran (40 mL) was added dropwise and the resulting reaction mixture stirred for 30 minutes. Methyl iodide (2.838 g; 20 mmol) was added and the reaction mixture stirred for 12 hours. The solvent was then re moved under reduced pressure and water (50 mL) was added. The reaction mixture was extracted with four 50 mL aliquots of ethyl acetate. The combined organic extracts were washed with brine solution (50 mL) dried over anhydrous magnesium sulfate and concentrated under reduced pressure. The crude product obtained was further purified by flash chromatography over silica gel using ethyl acetate as eluant to obtain 1.8 g of compound no. 1570R (yield=61%).

EXAMPLE 3

This example illustrates a method of synthesis for inventive compound no. 4544R (see above for chemical name and structure). A 250 mL r.b. flask fitted with a dropping funnel and a drying tube was charged with a solution of lisofylline (2.8 g, 10 mmol) in tetrahydrofuran (40 mL), triethylamine (10 mL) and N,N-dimethylaminopyridine (100 mg). The reaction flask was cooled to 10° C. and pivolyl chloride (3 mL, 24 mmol) was added dropwise and stirred for 24 hours. Water (50 mL) was added and the reaction mixture was extracted with four 50 mL aliquots of ethyl acetate. The combined organic extracts were washed with water (50 mL), brine solution (50 mL), dried over anhydrous magnesium sulfate and concentrated under reduced pressure. The crude product obtained was further purified by flash chromatography over silica gel using ethyl acetate as eluant, producing 2.4 g of inventive compound no. 4544R (yield=67%).

EXAMPLE 4

This example illustrates a method of synthesis for inventive compound no. 4545R (see above for chemical name and structure). A 250 mL r.b. flask fitted with a dropping funnel and a drying tube was charged with a solution of lisofylline (2.8 g, 10 mmol) in tetrahydrofuran (40 mL), triethylamnine (10 mL) and N,N-dimethylaminopyridine (100 mg). The reaction flask was cooled to 10° C. and benzoyl chloride (2.1 g; 1.74 mL, 15 mmol) was added dropwise. The resulting mixture was stirred for 24 hours. Water (50 mL) was added and the reaction mixture was extracted with four 50 mL aliquots of ethyl acetate. The combined organic extracts were washed with water (50 mL), cold dilute hydrochloric acid (50 mL) and brine solution (50 mL); dried over anhydrous magnesium sulfate; and concentrated under reduced pressure. The crude product obtained was further purified by flash chromatography over silica gel using ethyl acetate as eluant, producing 3.0 g of inventive compound no. 4545R (yield 78%).

EXAMPLE 5

This example illustrates a method of synthesis for inventive compound no. 4546R (see above for chemical name and structure). A 250 mL r.b. flask, fitted with a dropping funnel and a drying tube, was charged with a solution of lisofylline (2.8 g, 10 mmol) in dichloromethane (40 mL) and triethylamine (10 mL). The reaction flask was cooled to 10° C. and methoxyacetyl chloride (1.63 g; 1.4 mL; 15 mmol)) was added dropwise and stirred for 24 hours. Water (50 mL) was added and the reaction mixture was extracted with four 50 mL aliquots of ethyl acetate. The combined organic extracts were washed with water (50 mL) and brine solution (50 mL), dried over anhydrous magnesium sulfate and concentrated under reduced pressure. The crude product obtained was then further purified by flash chromatography over silica gel using hexane(20%)/ethyl acetate as eluant, resulting in 2.0 g of compound no. 4546R (yield=57%).

EXAMPLE 6

This example illustrates a method of synthesis for inventive compound no. 4547R (see above for chemical name and structure). A 250 mL two-necked flask fitted with an argon inlet and a septum was charged with (95%) sodium hydride (360 mg; 15 mmol). A solution of lisofylline (2.8 g, 10 mmol) in tetrahydrofuran (40 mL) was added dropwise and stirred for 30 minutes. Chloromethylpivalate (2.26 g; 15 mmol) was added and a resulting reaction mixture was refluxed for 8 hours. The solvent was then removed under reduced pressure. Water (50 mL) was slowly added at room temperature and the reaction mixture was extracted with four 50 mL aliquots of ethyl acetate. The combined organic extracts were washed with brine solution (50 mL), dried over anhydrous magnesium sulfate and concentrated under reduced pressure. The crude product obtained was further purified by flash chromatography over silica gel using ethyl acetate as eluant, resulting in 2.9 g of inventive compound no. 4547R (yield=74%).

EXAMPLE 7

This example illustrates a method of synthesis for inventive compound no. 4570R (see above for chemical name and structure). A 250 mL r.b. flask, fitted with a dropping funnel and a drying tube, was charged with a solution of lisofylline (1.4 g, 5 mmol) in dichlorornethane (20 mL) and triethylamnine (5 mL). The reaction flask was cooled to 10° C. and 3,4,5-trimethoxybenzoyl chloride. (1.15 g; 5 mmol) was added dropwise. The resulting reaction mixture was stirred for 24 hours. Water (50 mL) was added and the reaction mixture was extracted with four 50 mL aliquots of ethyl acetate. The combined organic extracts were washed with water (50 mL), cold dilute hydrochloric acid (50 mL) and brine solution (50 mL), dried over anhydrous magnesium sulfate and concentrated under reduced pressure. The crude product obtained was further purified by flash chromatography over silica gel using ethyl acetate/20% hexane as eluant to obtain 2.0 g of compound no. 4570R (yield=57%).

EXAMPLE 8

This example illustrates a method of synthesis for inventive compound no. 4571R (see above for chemical name and structure). A 250 mL r.b. flask, fitted with a dropping funnel and a drying tube, was charged with a solution of lisofylline (1.4 g, 5 mmol) in dichloromethane (20 mL) and triethylamine (5 mL). The reaction flask was cooled to 10° C. and trans-cinnamoyl chloride (1.0 g; 6 mmol) was added in portions and stirred for 24 hours. Water (50 mL) was added and the reaction mixture was extracted with four 50 mL aliquots of ethyl acetate. The combined organic extracts were washed with water (50 mL) and brine solution (50 mL), dried over anhydrous magnesium sulfate and concentrated under reduced pressure. The crude product obtained was further purified by flash chromatography over silica gel using an hexane(10%)/ethyl acetate as eluant, resulting in the 1.6 g of compound no. 4571R (yield=78%).

19

EXAMPLE 9

This example illustrates a method of synthesis for inventive compound no. 4572R (see above for chemical name and structure). A 250 mL r.b. flask, fitted with a dropping funnel and a drying tube, was charged with a solution of lisofylline (1.4 g, 5 mmol) in dichloromethane (20 mL), triethylamine (5 mL)) and N,N-dimethylaminopyridine (100 mg). The reaction flask was cooled to 10° C. and isobutyric anhydride (1.58 g; 1.65 mL; 10 mmol) was added dropwise, the resulting mixture stirred for 24 hours. The reaction was quenched by the addition of methanol (5 mL), followed by water (50 mL). The reaction mixture was extracted with four 50 mL aliquots of ethyl acetate and the combined organic extracts were washed with water (50 mL) and brine solution (50 mL), dried over anhydrous magnesium sulfate and concentrated under reduced pressure. The crude product obtained was further purified by flash chromatography over silica gel using ethyl acetate as eluant to obtain 1.6 g of compound no. 4572R (yield=91%).

EXAMPLE 10

This example illustrates a method of synthesis for inventive compound no. 4573R (see above for chemical name and structure). A 250 mL r.b. flask, fitted with a dropping funnel and a drying tube, was charged with a solution of lisofylline (1.4 g, 5 mmol) in dichloromethane (20 mL), triethylamine (5 mL) and N,N-dimethylaminopyridine (100 mg). The reaction flask was cooled to 10° C. and butyric anhydride (1.58 g; 1.65 mL; 10 mmol) was added dropwise and stirred for 24 hours. The reaction was quenched by the addition of methanol (5 mL) followed by water (50 mL). The reaction mixture was extracted with four 50 mL aliqouts of ethyl acetate. The combined organic extracts were subsequently washed with water (50 mL) and brine solution (50 mL), dried over anhydrous magnesium sulfate and concentrated under reduced pressure. The crude product obtained was further purified by flash chromatography over silica gel using ethyl acetate as eluant, resulting in 1.48 g of compound no. 4573R (yield=87%).

EXAMPLE 11

This example illustrates a method of synthesis for inventive compound no. 4574R (see above for chemical name and structure). A 250 mL r.b. flask, fitted with a dropping funnel and a drying tube, was charged with a solution of lisofylline (1.4 g, 5 mmol) in dichloromethane (20 mL) and triethylamine (5 mL). The reaction flask was cooled to 10° C. and decanoyl chloride (1.14 g; 6 mmol)) was added in portions. The resulting mixture was stirred for 24 hours. Water (50 mL) was added and the reaction mixture was extracted with four 50 mL aliquots of ethyl acetate. The combined organic extracts were washed with water (50 mL) and brine solution (50 mL), dried over anhydrous magnesium sulfate and concentrated under reduced pressure. The crude product obtained was further purified by flash chromatography over silica gel using an hexane(20%)/ethyl acetate as eluant to obtain 1.6 g of compound no. 4574R (yield=74%).

EXAMPLE 12

This example illustrates a method of synthesis for inventive compound no. 4575R (see above for chemical name and structure). A 250 mL r.b. flask fitted with a dropping funnel and a drying tube was charged with a solution of lisofylline (1.4.g, 5 mmol) in dichloromethane (20 mL), triethylamine (5 mL) and N,N-dimethylaminopyridine (100 mg). The reaction flask was cooled to 10° C. and propionic anhydride (0.79 g; 6 mmol) was added dropwise and stirred for 24 hours. The reaction was quenched by the addition of methanol (5 mL), followed by water (50 mL). The reaction mixture was extracted with four 50 mL aliqouts of ethyl acetate and the combined organic extracts were washed with water (50 mL) and brine solution (50 mL), dried over anhydrous magnesium sulfate and concentrated under reduced pressure. The crude product obtained was further purified by flash chromatography over silica gel using ethyl acetate as eluant to obtain 1.2 g of inventive compound no. 4575R (yield=71%).

EXAMPLE 13

This example illustrates a method of synthesis for inventive compound no. 4576R (see above for chemical name and structure). A 250 mL r.b. flask fitted with a dropping funnel and a drying tube was charged with a solution of lisofylline (1.40 g, 5 mmol) in ethyl acetate (20 mL), triethylamine (1.4 mL; 10 mmol) and N,N-dimethylaminopyridine (122 mg; 1 mmol). The reaction flask was cooled to 10° C. and succinic anhydride (0.6 g, 6 mmol) was added. The resulting mixture was stirred for 24 hours. 2N hydrochloric acid (10 mL) was added and the reaction mixture was extracted with four 50 mL aliquots of dichloromethane. The combined organic extracts were washed with brine solution (50 mL), dried over anhydrous magnesium sulfate and concentrated under reduced pressure. The crude product obtained was further purified by flash chromatography over silica gel using a 5% methanol/ethyl acetate eluant, producing 1.0 g of inventive compound no. 4576R (yield=53%).

EXAMPLE 14

This example illustrates a method of synthesis for inventive compound no. 4577R (see above for chemical name and structure). A 250 mL two-necked flask, fitted with an argon inlet and a septum, was charged with (95%) sodium hydride (180 mg; 7.5 mmol). A solution of lisofylline (1.4 g, 5 mmol) in tetrahydrofuran (20 mL) was added dropwise and the reaction mixture stirred for thirty minutes. Benzyl bromide (1.28 g; 0.895 mL; 7.5 mmol) was added and the reaction mixture was refluxed for 8 hours. The solvent was then removed under reduced pressure and water (50 mL) was added at room temperature slowly. The reaction mixture was extracted with four 50 mL aliquots of ethyl acetate. The combined organic extracts were washed with brine solution (50 mL), dried over anhydrous magnesium sulfate, and concentrated under reduced pressure. The crude product obtained was further purified by flash chromatography over silica gel using ethyl acetate as eluant to obtain 1.0 g of compound no. 4577R (yield=1.0 g (54%).

EXAMPLE 15

This example illustrates a method of synthesis for inventive compound no. 5500R (see above for chemical name and structure). A 100 mL two-necked flask, fitted with an argon inlet and a septum, was charged with a solution of lisofylline (1.4 g, 5 mmol) N-carbobenzyloxyglycine (1.225 g; 6 mmol) and N,N-dimethylaminopyridine (488.7 mg; 4 mmol) in dry dichloromethane (20 mL). A 1M solution of dicyclohexylcarbodiimide (6 mL; 6 mmol) in dichloromethane was added and stirred for 16 hours. The precipitated urea was removed by filteration and the residue was washed with dichloromethane (50 mL). The combined filterate was concentrated under reduced pressure and the crude product obtained was further purified by flash chromatography over silica gel using ethyl acetate as eluant to obtain 1.8 g of 1-(5-(R)-hydroxyhexyl)-3,7-dimethylxanthine N-benzyloxycarbamoyl glycinate ester (yield=76%).

A solution of 1-(5-(R)-hydroxyhexyl)-3,7-dimethylxanthine N-benzyloxycarbamoyl glycinate ester (1.8 g; 3.82 mmol), prepared above, in ethanol (50 mL) was hydrogenated in presence of 10% palladium on carbon (400 mg) at room temperature for 12 hours. The reaction mixture was then filtered and concentrated under reduced pressure. The crude product was then redissolved in dichloromethane (15 mL) and treated with 1M solution of hydrogen chloride in ether (5 mL). The solvent was removed under reduced pressure to obtain 1.05 g of compound no. 5500R (yield=74%).

EXAMPLE 16

This example illustrates a method of synthesis for inventive compound no. 5501R (see above for chemical name and structure). A 100 mL two-necked flask, fitted with an argon inlet and a septum, was charged with a solution of lisofylline (1.4 g, 5 mmol) N-carbobenzyloxy-L-isoleucine (1.6 g; 6 mmol) and N,N-dimethylaminopyridine (488.7 mg; 4 mmol) in dry dichlorometiane (20 mL). A 1M solution of dicyclohexylcarbodiimide (6 mL; 6 mmol) in dichloromethane was added and stirred for 16 hours. The precipitated urea was removed by filteration and the residue was washed with dichloromethane (50 mL). The combined filterate was concentrated under reduced pressure and the crude product obtained was further purified by flash chromatography over silica gel using ethyl acetate as eluant to obtain 2.4 g of 1-(5(R)-hydroxyhexyl)-3,7-dimethylxanthine N-benzyloxycarbamoyl-L-isoleucinate ester (yield=91%).

A solution of 1-(5-(R)-hydroxyhexyl)-3,7-dimethylxanthine N-benzyloxycarbamoyl-L-isoleucinate ester (2.24 g; 4.25 mmol), prepared above in ethanol (50 mL) was hydrogenated in the presence of 10% palladium on carbon (400 mg) at room temperature for 12 hours. The reaction mixture was then filtered and concentrated under reduced pressure. The crude product was then redissolved in dichloromethane (15 mL) and treated with 1M solution of hydrogen chloride in ether (5 mL). The solvent was removed under reduced pressure to obtain 1.2 g of compound no. 5501R (yield=71%).

EXAMPLE 17

This example illustrates a method of synthesis for inventive compound no. 5502R (see above for chemical name and structure). A 100 mL two-necked flask, fitted with an argon inlet and a septum, was charged with a solution of lisofylline (1.4 g, 5 mmol) N-carbobenzyloxy-L-valine (1.5 g; 6 mmol) and N,N-dimethylaminopyridine (488.7 mg; 4 mmol) in dry dichloromethane (20 mL). A 1M solution of dicyclohexylcarbodiimide (6 mL; 6mmol) in dichloromethane was added and stirred for 16 hours. The precipitated urea was removed by filteration and the residue was washed with dichloromethane (50 mL). The combined filterate was concentrated under reduced pressure and the crude product obtained was further purified by flash chromatography over silica gel using ethyl acetate as eluant to obtain 1.9 g of 1-(5-(R)-hydroxyhexyl)-3,7-dimethylxanthine N-benzyloxycarbamoyl-L-valinate ester (yield=1.9 g 76%).

A solution of 1-(5-(R)-hydroxyhexyl)-3,7-dimethylxanthine N-benzyloxycarbamoyl-L-valinate ester (1.8 g; 3.5 mmol) in ethanol (50 mL) was hydrogenated in presence of 10% palladium on carbon (400 mg) at room temperature for 12 hours. The reaction mixture was then filtered and concentrated under reduced pressure. The crude product was then redissolved in dichloromethane (15 mL) and treated with 1M solution of hydrogen chloride in ether (4 mL). The solvent was removed under reduced pressure, resulting in 1.2 g of inventive compound no. 5502R (yield=83%).

EXAMPLE 18

This example illustrates a method of synthesis for inventive compound no. 5503R (see above for chemical name and structure). A 250 mL r.b. flask fitted with a dropping funnel and a drying tube was charged with a solution of lisofylline (1.40 g, 5 mmol) in dichloromethane (30 mL), triethylamine (1.4 mL, 10 mmol) and NN-dimethylaminopyridine (122 mg; 1 mmol). The reaction flask was cooled to 10° C., after which phthalic anhydride (0.89 g, 6 mmol). The resulting reaction mixture was stirred for 24 hours. 2N hydrochloric acid (10 mL) was added and the reaction mixture was extracted with four 50 mL aliquots of dichloromethane. The combined organic extracts were washed with brine solution (50 mL), dried over anhydrous magnesium sulfate and concentrated under reduced pressure. A crude product from this concentration was further purified by flash chromatography over silica gel using a 5% methanol/ethyl acetate eluant. Recrystalization of the purified product from ethyl acetate produced 1.4 g of compound 5503 (yield=65%).

EXAMPLE 19

This example illustrates a method of synthesis for inventive compound no. 5504R (see above for chemical name and structure). 4-benzyloxybenzoic acid was first prepared (paragraph A below) and then used to make compound 5504 (paragraph B below).

A) 4-benzyloxybenzoic acid:

A solution of 4-hydroxybenzoic acid (5.52 g; 40 mole), benzyl bromide (11.89 mL; 0.1 mol) and tricaprylylmethylammonium chloride (100 mg, Aliquat 336® Henkel Corporation) in methanol (50 mL) was refluxed in presence of potassium carbonate (16.52 g) for 12 hours. The reaction mixture was then poured slowly into a solution of 2N hydrochloric acid solution. The precipitated acid was filtered, dried and recrystallized from hexane/ethyl acetate to give 5 g of 4-benzyloxybenzoic acid (yield=55%).

B) 1-(5-(R)-(4'-benzyloxybenzoyloxy)hexyl)-3,7-dimethylxanthine:

A 100 mL two-necked flask, fitted with an argon inlet and a septum, was charged with a solution of lisofylline (2.8 g, 10 mmol), 4-benzyloxybenzoic acid, prepared above, (2.73 g; 1.2 mmol) and N,N-dimethylaminopyridine (977 mg; 8 mmol) in dry dichloromethane (30 mL). A 1M solution of dicyclohexylcarbodiimide (12 mL; 12 mmol) in dichloromethane was added and the resulting reaction mixture stirred for 16 hours. The precipitated urea was removed by filteration and the residue was washed with dichloromethane (50 mL). The combined filterate was concentrated under reduced pressure and the crude product obtained was further purified by flash chromatography over silica gel using an ethyl acetate/30% hexane eluant, resulting in 4.45 g 1-(5-(R)-(4'-benzyloxybenzoyloxy)hexyl)-3,7-dimethylxanthine (yield=91%).

A solution of 1-(5-(R)-(4'-benzyloxybenzoyloxy)hexyl)-3,7-dimethylxanthine (4.48 g) in ethanol (50 mL) was hydrogenated in presence of 10% palladium carbon (800 mg) at room temperature for 12 hours. The reaction mixture was then filtered and concentrated under reduced pressure to obtain 3.2 g of compound no. 5504R (yield=3.2 g 88%).

EXAMPLE 20

This example illustrates a method of synthesis for inventive compound no. 5527R (see above for chemical name and structure). A 250 mL r.b. flask, fitted with a dropping funnel and a drying tube, was charged with a mixture of lisofylline (2.8 g, 10 mmol), isatoic anhydride (2 g, 12 mmol), N,N-dimethylaminopyridine (1.2 g 10 mmol) and dimethylformamide (25 mL). The reaction flask was heated to 80° C. for 4 hours. After cooling to room temperature, water 50 mL) was added and the reaction mixture was extracted with four 50 mL aliquots of ethyl acetate/10% methanol. The combine organic extracts were washed with water (50 mL) and brine solution (50 mL), dried over anhydrous magnesium sulfate and concentrated under reduced pressure. The crude product obtained was further purified by flash chromatography over silica gel using ethyl acetate as eluant, resulting in 0.72 g of compound no. 5527R (yield=18%).

EXAMPLE 21

This example illustrates a method of synthesis for inventive compound no. 5531R (see above for chemical name and structure). A 250 mL two-necked flask, fitted with an argon inlet and a septum, was charged with (95%) sodium hydride (144 mg; 6 mmol). A solution of lisofylline (1.4 g, 5 mmol) in tetrahydrofuran (20 mL) was added dropwise and stirred for 30 minutes. N,N-dimethylcarbomyl chloride (0.645 g; 6 mmol) was added and the reaction mixture was refluxed for 12 hours. The reaction mixture was then cooled back to room temperature, and water (50 mL) was added slowly. The reaction mixture was then extracted with four 50 mL aliquots of ethyl acetate. The combined organic extracts were washed with brine solution (50 mL), dried over anhydrous magnesium sulfate and concentrated under reduced pressure. The crude product obtained was further purified by flash chromatography over silica gel using 50% dichloromethane/49% hexane/1% methanol as eluant, which resulted in 1.3 g of compound no. 5531R (yield=74%).

EXAMPLE 22

This example provides data on in vitro metabolism of lisofylline, its corresponding opposite enantiomer, 1-[5-(S)-hydroxyhexyl]-3,7-dimethylxanthine, and stability of the inventive compounds nos. 1515R, 1570R, 4544R, 4545R, 4546R and 4547R, when incubated with samples of human whole blood.

A stereoselective HPLC method was used to determine concentrations of lisofylline and its corresponding opposite isomer. Separation of analytes as their phenylisocyanate derivatives was accomplished by HPLC on a Chiracel OJ (25×0.46 cm, 5 $\mu$) analytical column with UV detection at 273 nm. The mobile phase was methanol/water/trifluoroacetic acid (95:4.5:0.5) delivered at a flow rate of 0.8 mL/minute with a run time of 30 minutes. The column temperature was set at 30° C. Data was collected using the Waters 860 Chromatography Data System with Expert Ease 3.2 software. Calibration was accomplished by a weighted 1/x.least squares regression analysis. Calculations were based on peak area ratios; Total-recovery of analytes [the combined R and S enantiomers of corresponding inventive compound and lisofylline and its corresponding S enantiomer)] in these experiments was 80%–85%.

Procedurally, whole human blood was obtained from healthy volunteers and collected into pre-wetted tubes with 3.8% sodium citrate as anticoagulant. The final concentration of inventive compounds in the incubation was 100 $\mu$M. Incubation time was 60 minutes for all tissues (bath temperature: 37° C.; shaker setting: 30 rpm). Samples were taken at the following time intervals: 0, 5, 15, 30 and 60 minutes. Enzymatic activity was arrested by pre-wetting the sample culture tubes with 50 mL of acetone, and cooling the sample tubes in ice.

Figure 2:
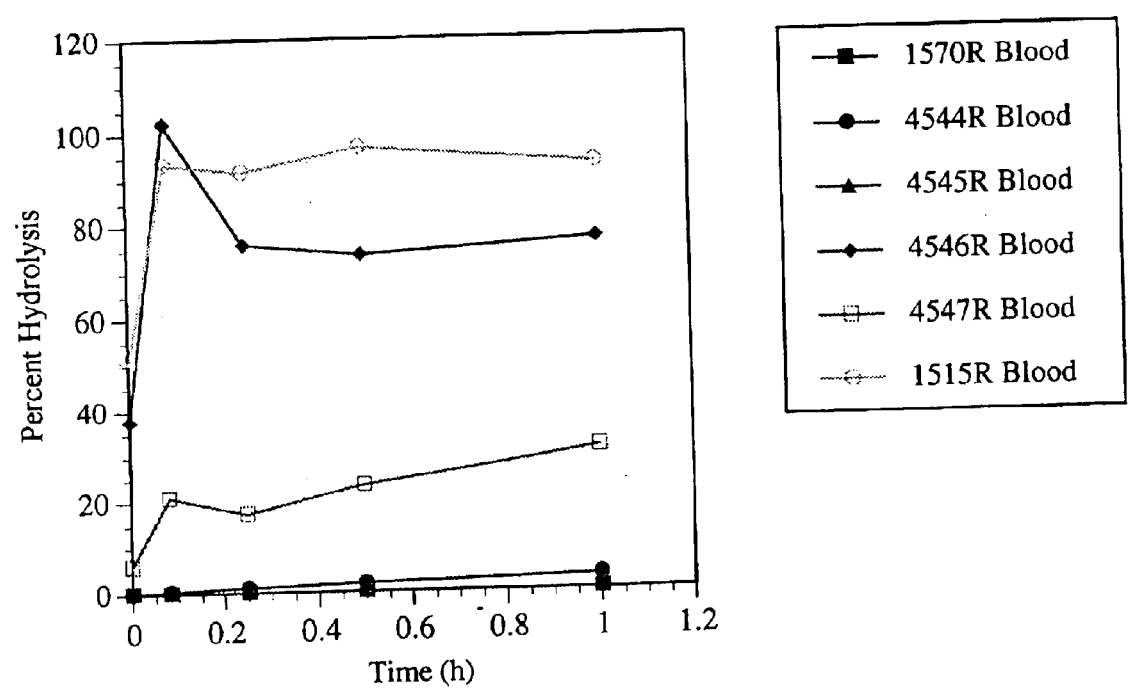
FIG. 2 illustrates the amount of hydrolysis of various prodrug compounds with whole human blood.

FIG. 2 reports results obtained in this assay, illustrating amounts of hydrolysis of various inventive compounds with whole human blood. The extent of hydrolysis is measured by the appearance of lisofylline and was measured by the stereoselective HPLC method described above. As shown by the data reported in FIG. 2, compounds 1570R, 4544R and 4545R are quite resistant to hydrolysis in incubations with whole human blood. In comparison, compounds nos. 1515R and 4546R are hydrolyzed quite readily under these conditions and compound no. 4547R has an hydrolysis rate between the most resistant compounds tested and those readily hydrolyzed, indicating that a specific rate of hydrolysis can be selected for a particular use of the compound.

EXAMPLE 23

This example provides data on the in vitro hydrolysis of representative inventive compounds in human intestinal homogenates.

Procedurally, homogenate was prepared in DMEM: F-12 Hams (50:50) with essential trace elements (commercial preparation), NaHCO$_3$ and HEPES (pH 7.0). Tissue was weighed to the nearest 0.1 mg and minced on an iced petri dish. Minced tissue was placed in an iced homogenizer (with 10 mL media) and disrupted with ten (10) strokes of a motorized Teflon pestle. The volume of homogenate was adjusted with the appropriate amount of media for each incubation set. Approximate protein concentration was 30 mg/mL. Final incubation volume per compound was 3 mL. Compound concentrations were identical to compound concentration used in Example 22. Lisofylline was incubated under the same conditions and concentration used for the inventive compounds tested to demonstrate recovery of lisofylline in the system.

The extent of hydrolysis was measured by the appearance of lisofylline and is measured by the stereoselective HPLC method described in Example 22, above.

Figure 3:
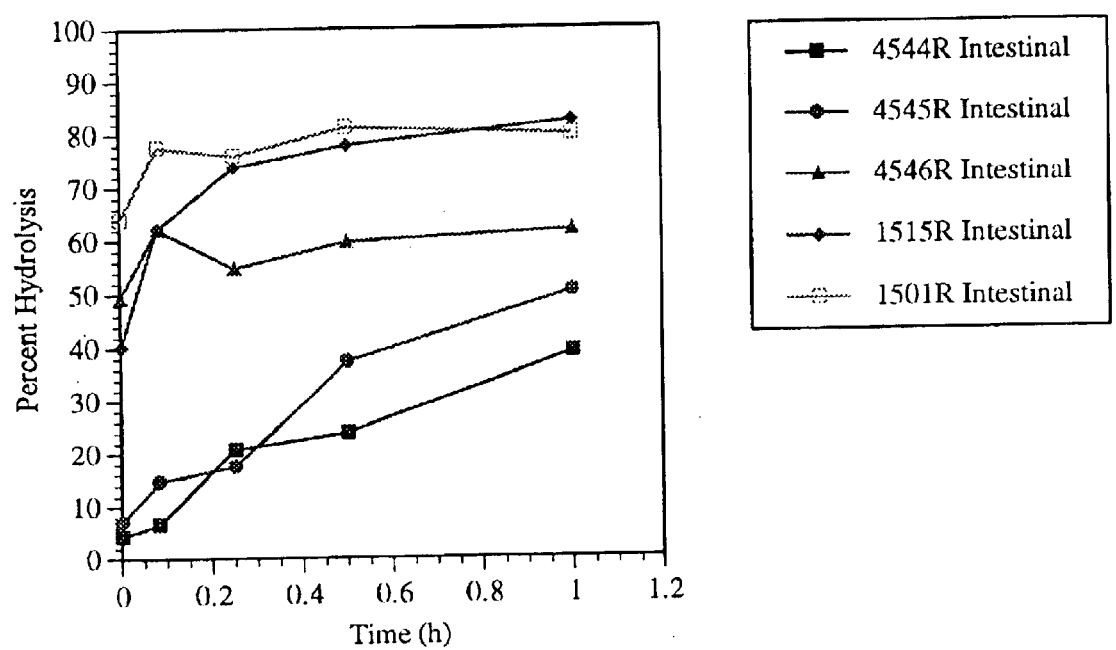
FIGS. 3 and 4 show rate of hydrolysis data of various inventive compounds in human intestinal homogenates.
Figure 4:
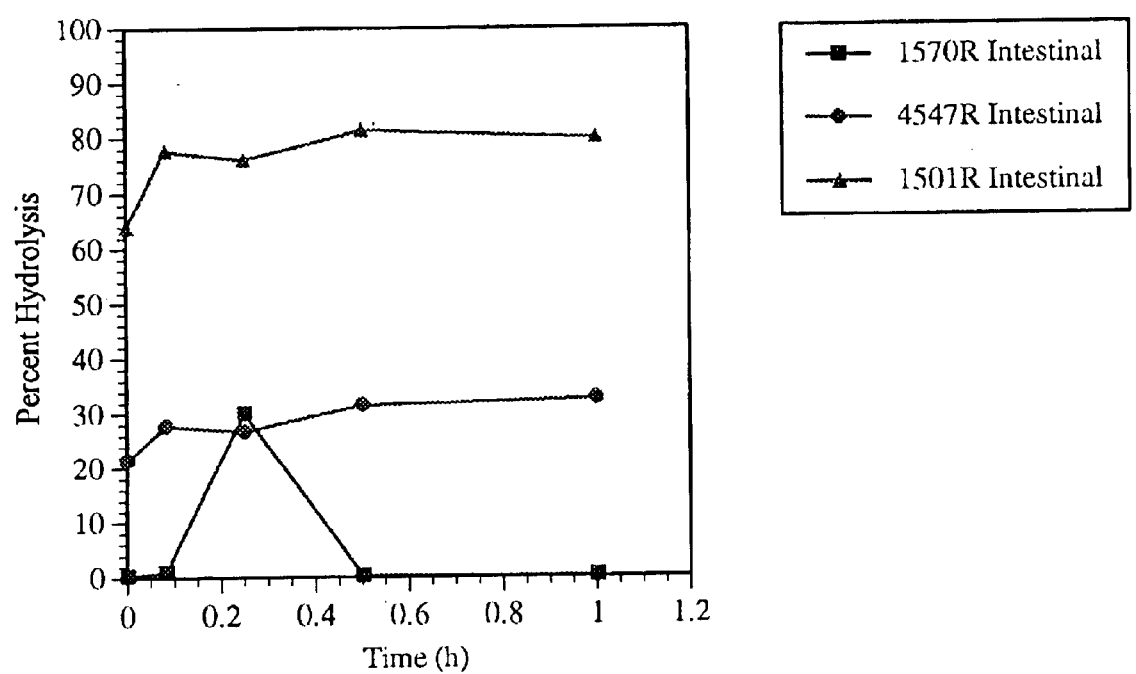

FIGS. 3 and 4 illustrate the hydrolysis of representative compounds in the presence of human intestinal homogenates. The compound most resistant to hydrolysis was 1570R, followed by 4544R and 4545R. Compound no. 4547R was hydrolyzed at an intermediate rate while 1515R and 4546R underwent rapid hydrolysis in comparison to other compounds tested. This trend is similar to that observed in whole human blood.

EXAMPLE 24

This example provides data on the in vitro hydrolysis of representative inventive compounds in human liver homogenates.

Homogenate was prepared in DMEM : F-12 Hams (50:50) with essential trace elements (commercial preparation), 14.3 mM NaHCO$_3$ and 15 mM HEPES (pH 7.0). Tissue was weighed to the nearest 0.1 mg and minced on an iced petri dish. Minced tissue was placed in an iced homogenizer (with 10 mL media) and disrupted with ten (10) strokes of a motorized Teflon pestle. The volume of homogenate was adjusted with the appropriate amount of media for each incubation set. Final incubation volume per inventive compound was 3 mL. Approximate protein concentration was 30 mg/mL. Incubation time, sampling rate and compound concentrations were the same as used for whole blood incubation, described in Example 22, above. Lisofylline was incubated in the same conditions as the inventive compounds to demonstrate recovery of lisofylline in the system.

Figure 5:
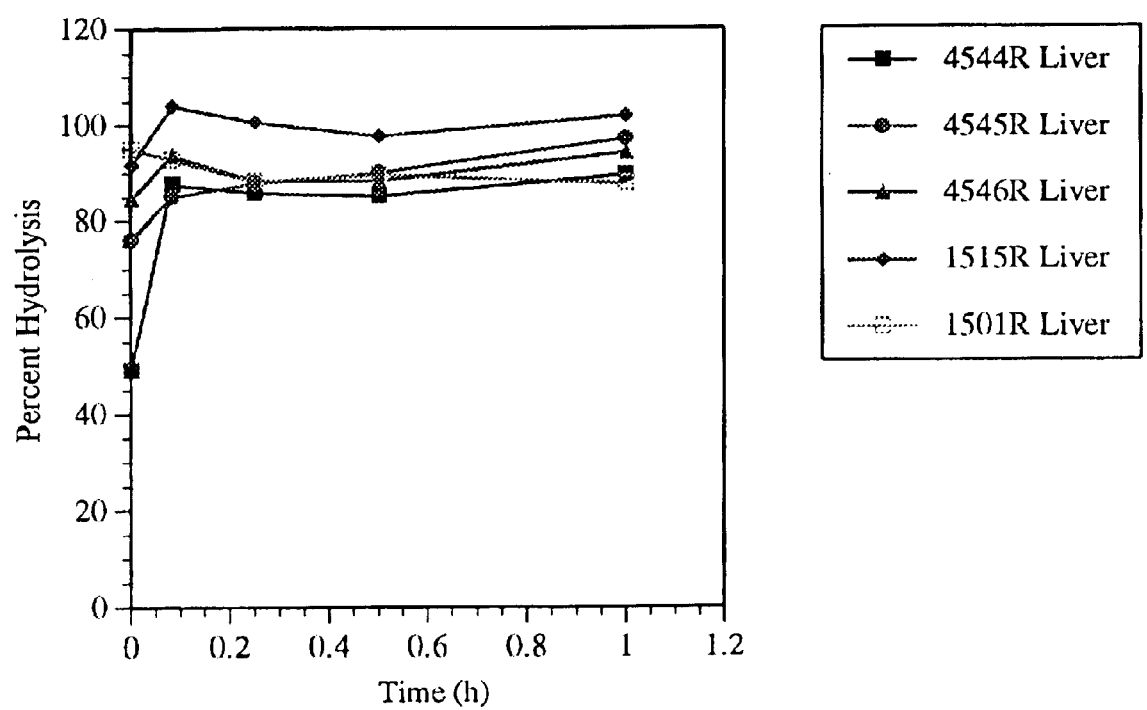
FIGS. 5 and 6 are plots of the rate of hydrolysis of inventive compound in human liver homogenates.
Figure 6:
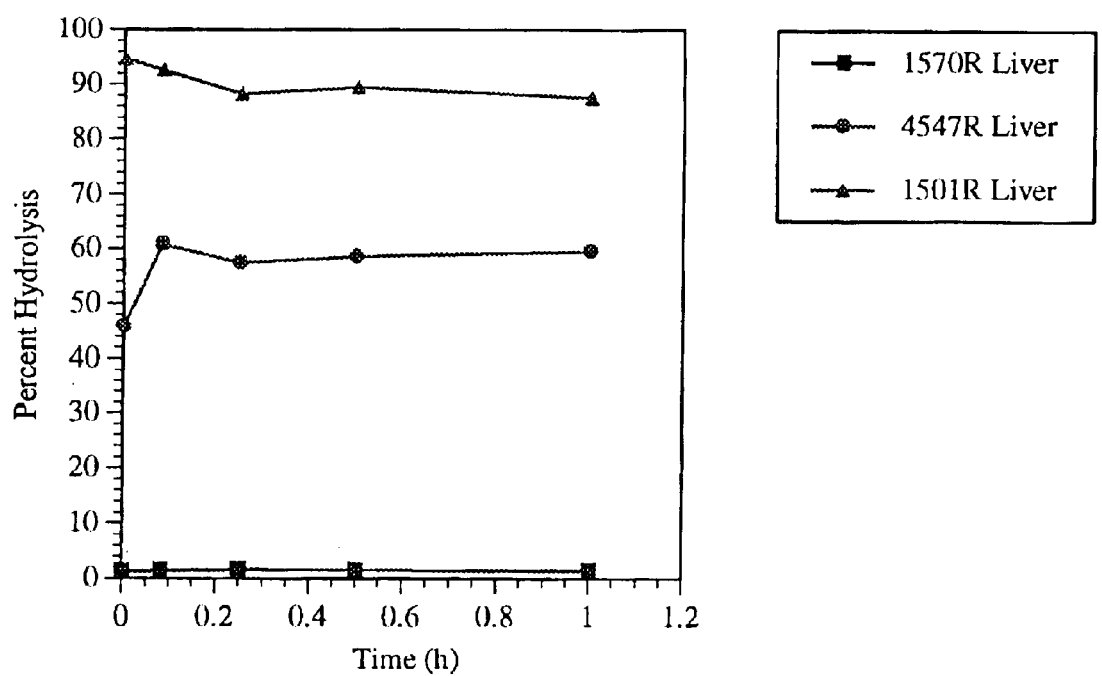
Figure 7:
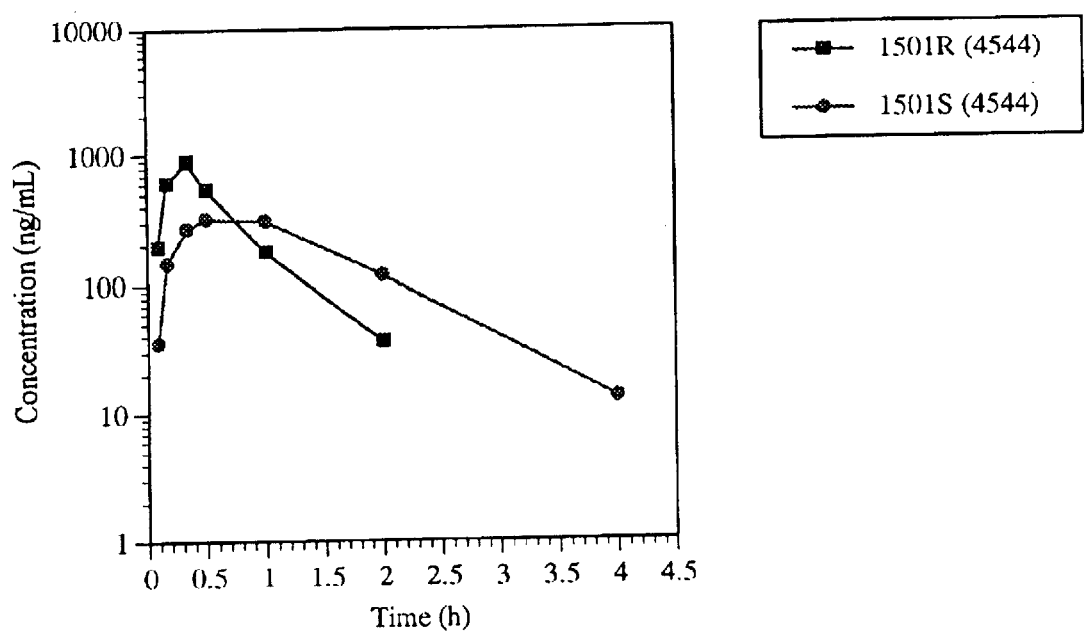
FIG. 7 is a plot of the concentrations of lisofylline and its corresponding S enantiomer in canine blood over time, after oral administration of inventive compound no. 4544R.

FIGS. 5 and 6 illustrate the hydrolysis of the various inventive compounds in the presence of human liver homogenates. As observed in the previous examples, the compound most resistant to hydrolysis is 1570R. A medium rate of hydrolysis was observed for compound no. 4547R and rapid hydrolysis, in comparison to other compounds, was observed for compounds nos. 1515R, 4544R, 4545R and 4546R. The rapid hydrolysis of the inventive compounds 4544 and 4545 by the liver homogenate illustrates their specific high hydrolytic potential in this tissue.

EXAMPLE 25

As the data provided in examples 22–24 were representative, predictive in vitro assays of conditions that a compound would experience upon oral administration, this example, showing in vivo results conducted in canine species, confirms that representative compounds of the inventive genus (specifically, inventive compounds nos. 4544, 4545 and 4576): 1) may increase the bioavailability of the compound (for systemic hydrolysis to the therapeutic lisofylline); 2) may maintain a higher ratio of concentration of lisofylline (the desired therapeutic compound) to concentration of the S enantiomer of lisofylline; and 3) may retain this ratio for a longer period of time.

Research has shown that the dog metabolizes lisofylline in a manner similar to humans; thus this representative assay is predictive of results which would be seen in oral administration of the inventive compounds in humans.

Procedurally, stereochemical HPLC analyses were conducted as outlined in example 22 above. Treatment of dogs (in duplicate) with various compounds was accomplished by administration of a single oral dose (10 mg/kg) via a mouth tube. The test compounds were first dissolved into water and dosed as solutions. Venous blood draws were conducted at follows: predose, and then 5, 10, 20, 30, 60, 120 and 240 minutes pose dose. The blood samples were centrifuged to obtain the plasma, which was drawn off and frozen at −70° C. until analyzed.

FIGS. 7–10 depict plasma levels of lisofylline and it corresponding S enantiomer in plasma of dogs that were treated with the inventive compound nos. 4544R, 4545R, 4576R and 4577R. From the data reported in these figures, the pharmacokinetics of lisofylline depend specifically on the chemical structure of a particular compound and its corresponding hydrolytic potential that was administered. In particular, the absolute amounts of target therapeutic, lisofylline, that are formed were dependent upon which specific compound was orally administered.

Using compound no. 4544R, the absolute canine blood levels of lisofylline are the most significant, at 1000 ng/mL. The level achieved with 4545R and 4577R represent intermediate blood levels at approximately 400 ng/mL. The lowest blood levels obtained for the compounds tested were 200 ng/mL for compound no. 4576R.

Due to the metabolic profile for lisofylline, an additional quantitative measure in evaluating the hydrolytic potential of the inventive compounds is a ratio of lisofylline to its corresponding S enantiomer (R:S ratio), which as confirmed by the data obtained also depends on the chemical entity administered and its structural chemistry.

Figure 8:
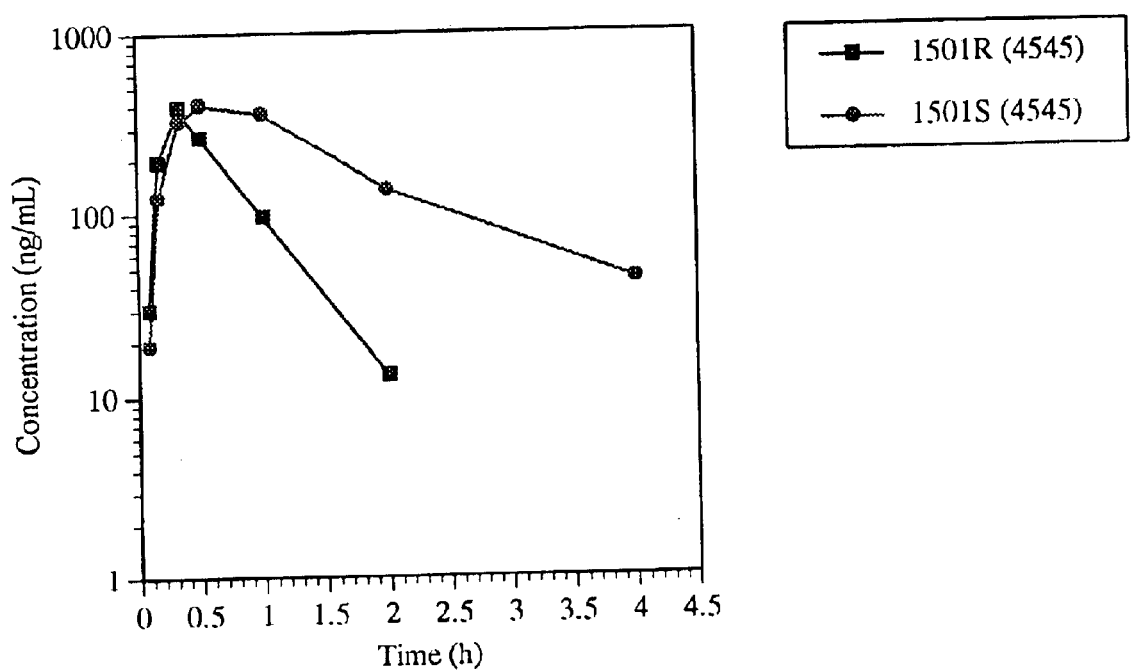
FIG. 8 is a plot of the concentrations of lisofylline and its corresponding S enantiomer in canine blood over time, after oral administration of inventive compound no. 4545R.
Figure 9:
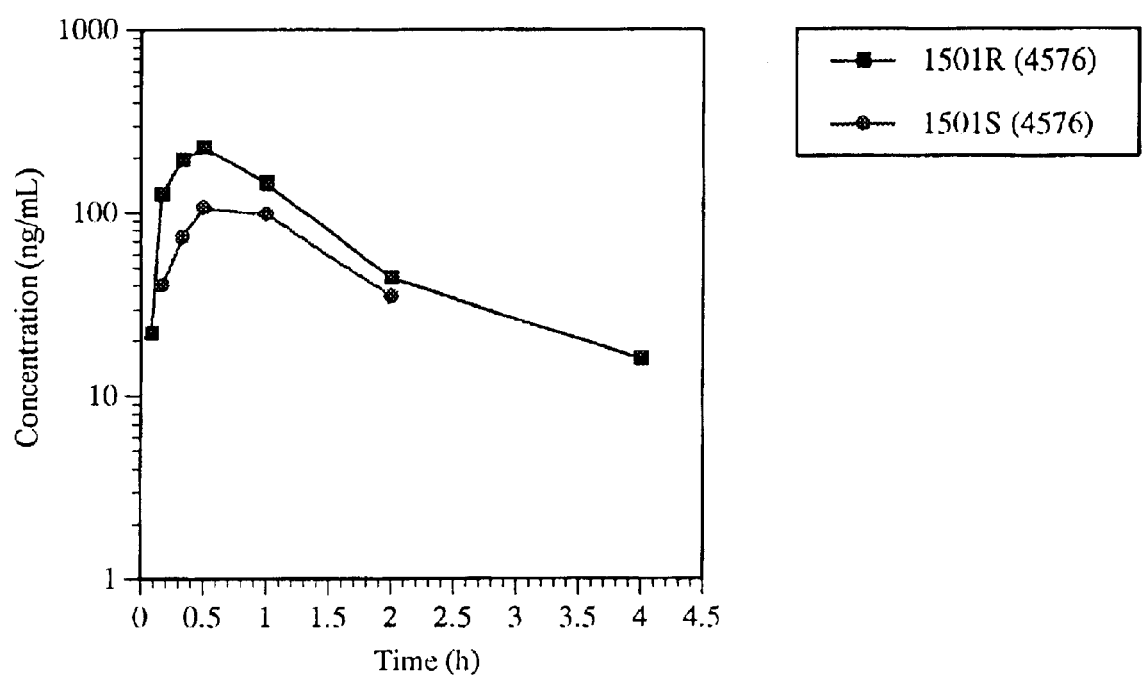
FIG. 9 is a plot of the concentrations of lisofylline and its corresponding S enantiomer in canine blood over time, after oral administration of inventive compound no. 4576R.
Figure 10:
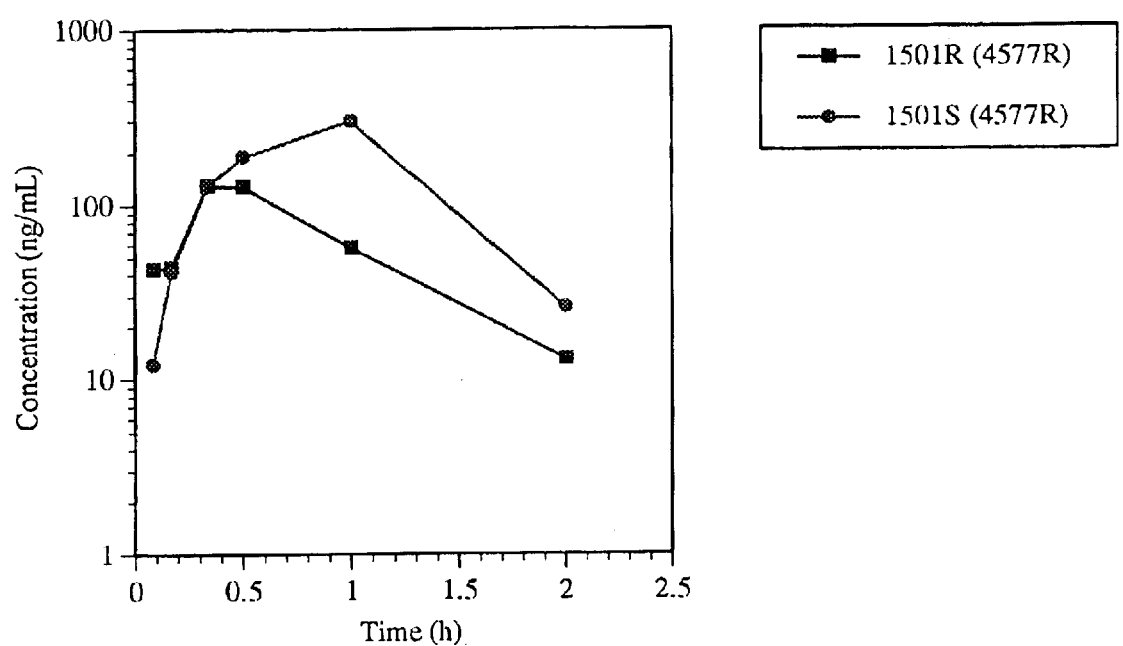
FIG. 10 is a plot of concentration of lisofylline and its corresponding S enantiomer over 2 hours in canine blood dosed with inventive compound no. 4577R.

In FIG. 8, the maximum concentrations of lisofylline and its S enantiomer are equal and appear about 0.25 hours after administration of inventive compound no. 4545. In FIG. 9, inventive compound no. 4576 results in a more significant and prolonged increase in the maximum concentration of the desired pharmaceutical lisofylline, as compared with its corresponding S enantiomer. The ratio of lisofylline to S enantiomer is approximately 1 at that point and drops thereafter. A comparison of FIGS. 8 with 7, 9 and 10 illustrates that an R:S ratio substantially greater than unity can be achieved with compounds nos. 4544R, 4576R and 4577R; however, compound no. 4545R suggests that the corresponding S enantiomer is present in greater quantities than lisofylline.

An additional property shown exclusively by compound no. 4576R is an increased lisofylline half-life. This characteristic is best illustrated by comparing the slope of the elimination phase of lisofylline in FIG. 9 against either FIG. 7 or 8. Also, in analyzing these data, compound no. 4577R exhibits an interesting feature, involving an evident delay in reaching a maximum blood concentration (Tmax). Administering compound no. 4577R as described above delays Tmax 1 hour. However, Tmax occurs much earlier (within 0.5 hour) using other representative compounds.

These data suggest that specific compounds have greater hydrolytic potential based on their chemical structure and exhibit certain desirable characteristics in this predictive metabolic profile.

We claim:

1. A compound having the following structure:

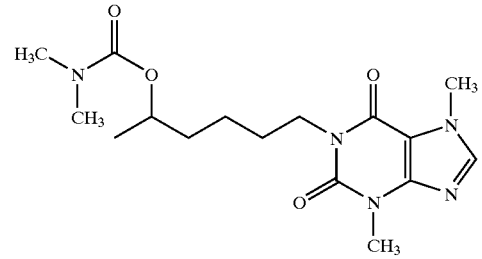

or a structure according to formula I:

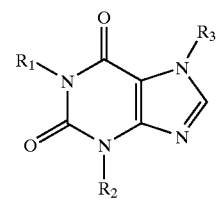

wherein $R_1$ has the formula II:

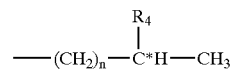

$R_2$ and $R_3$ are independently $C_{(1-12)}$ alkyl, optionally, $R_2$ having one or two nonadjacent carbon atoms of the $C_{(1-12)}$ alkyl being replaced by an oxygen atom; and wherein:

C* is a chiral carbon atom;

n is four;

R₄ is a naturally occurring amino acid attached by an oxygen atom to the chiral carbon atom C* by an ester linkage, —O—X—(R₅)ₘ; m being two or three, depending on valence, and X being selected from the group consisting of C, P or S; wherein one R₅ is =O and any other R₅ is a member independently selected from Group Q, and Group Q consists of:

hydroxyl group;

substituted or unsubstituted $C_{(3-10)}$ allyl, $C_{(2-10)}$ alkenyl, $C_{(1-10)}$ alkynyl, $C_{(1-10)}$ alkoxyl, $C_{(1-10)}$ oxoalkyl, $C_{(1-10)}$ carboxyalkyl, $C_{(1-10)}$ hydroxyalkyl, or substituted $C_{(1-2)}$ alkyl group;

—OR₆, R₆ being a substituted or unsubstituted $C_{(1-10)}$ alkyl, $C_{(2-10)}$ alkenyl, $C_{(2-10)}$ alkynyl, or $C_{(1-10)}$ oxoalkyl;

substituted or unsubstituted heterocylic group, attached to X through an atom within the ring, having one or two rings, each ring containing from four to seven atoms, wherein the heteroatom(s) of said heterocyclic group is 1 or 2 nitrogens; and substituted or unsubstituted carbocyclic group that is attached to X through a carbon atom within a ring, having one or two rings, each ring containing four to seven atoms, wherein the substituents of said substituted carbocyclic group are selected from the group consisting of amino, $C_{(2-6)}$ alkenyl, $C_{(1-6)}$ alkyl, $C_{(1-6)}$ alkoxyl, $C_{(1-6)}$ hydroxyalkyl, hydroxyl, $C_{(1-6)}$ oxoalkyl, azido, cyano, $C_{(2-6)}$ mono- or di-haloalkyl, isocyano, isothiocyano, imino, a chlorine atom, a bromine atom, a fluorine atom and an oxygen atom.

2. The compound of claim 1, wherein the amino acid is selected from the group consisting of: alaninyl, argininyl, asparaginyl, aspartyl, cysteinyl, glutaminyl, glutamyl, glycinyl histidinyl, isoleucinyl, leucinyl, lysinyl, methioninyl, phenylalaninyl, prolinyl, serinyl, threoninyl, tryptophanyl, tyrosinyl and valinyl.

3. The compound of claim 1, wherein X is C.

4. The compound of claim 1, wherein substituents for the substituted $C_{(1-10)}$ alkyl, $C_{(2-10)}$ alkenyl, $C_{(2-10)}$ alkynyl, $C_{(1-10)}$ alkoxyl, $C_{(1-10)}$ oxoalkyl, and heterocyclic groups are selected from the group consisting of amino, $C_{(2-6)}$ alkenyl, $C_{(1-6)}$ alkyl, $C_{(1-6)}$ alkoxyl, $C_{(1-6)}$ hydroxyalkyl, $C_{(1-6)}$ oxoakyl, azido, cyano, $C_{(1-6)}$ haloalkyl, isocyano, isothiocyano, imino, alkylthio, chlorine, bromine, fluorine and oxygen atom.

5. The compound of claim 4, wherein the $C_{(1-6)}$ haloalkyl is a mono-, di- or tri haloalkyl and the $C_{(1-6)}$ alkoxyl is a methoxy or ethoxy group.

6. The compound of claim 1, wherein one or two, non-adjacent carbon atoms of R₂ are replaced with oxygen atoms.

7. The compound of claim 1, wherein the carbocyclic or heterocyclic group is selected from the group consisting of phenyl, biphenyl, cyclohexyl, cyclohexenyl, cyclopentyl, cyclopentenyl, cyclopentanedionyl, napthlalenyl, phenolyl, quinonyl, cyclobutyl, cycloheptyl, cycloheptenyl, indanyl, indenyl, decalinyl, resorcinolyl, tetralinyl, α-tetralonyl, 1-indanonyl, cyclohexanedionyl, cyclopentanedionyl, phthalimidyl, homophthalimidyl, quinazolinonyl, glutarimidyl, piperidonyl, succinimidyl, dimethoxyphenyl, methyildihydrouracilyl, methyluracilyl, methylthyminyl, piperidinyl, and dihydroxybenzenyl.

8. The compound of claim 1, wherein the other R₅, other than =O, is trimethoxy-substituted phenyl.

9. The compound of claim 1, wherein R₄ is glycinyl, isoleucinyl or valinyl.

10. The compound of claim 1, wherein said from:

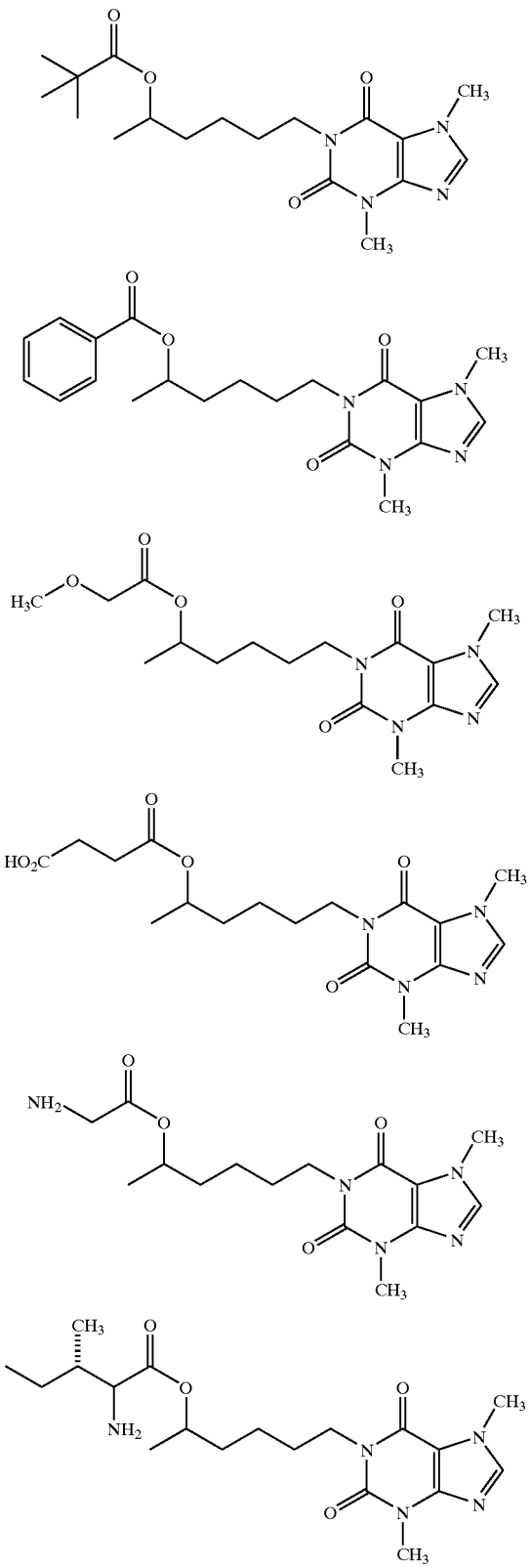

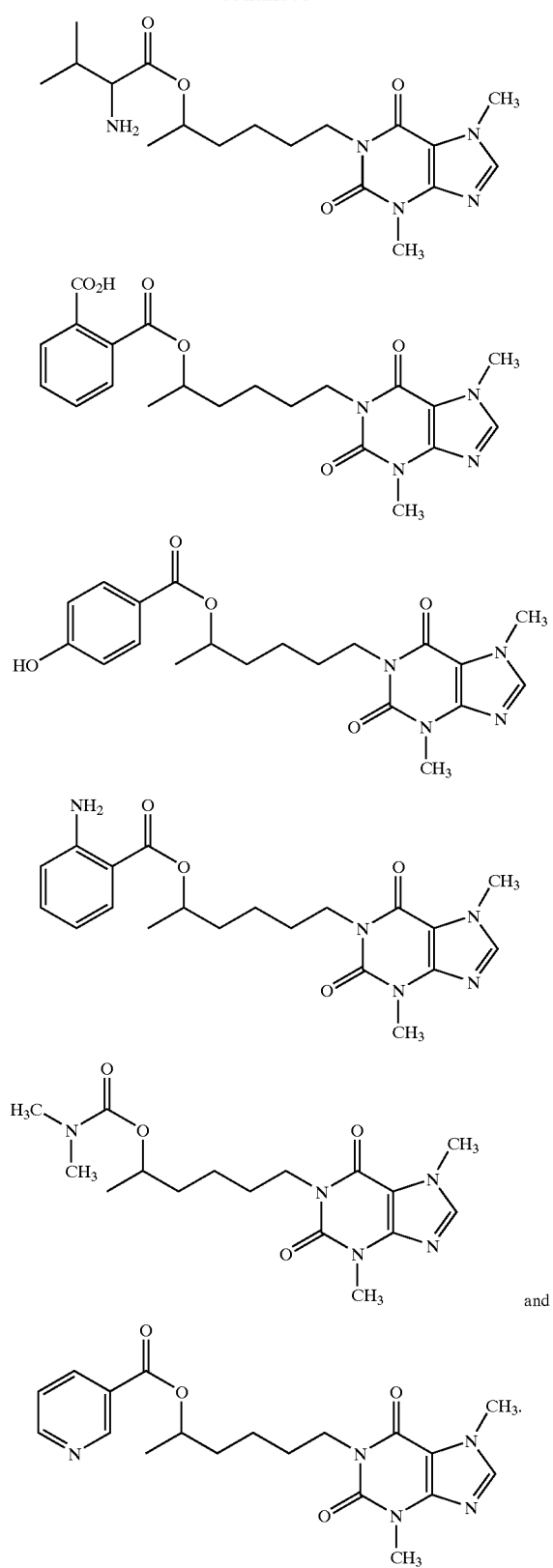

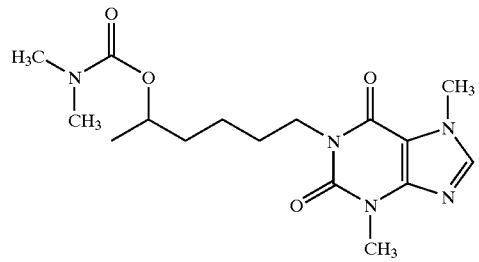

or a structure according to formula I:

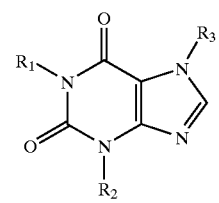

wherein $R_1$ has the formula II:

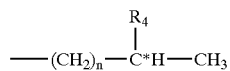

$R_2$ and $R_3$ are independently $C_{(1-12)}$ alkyl, optionally, $R_2$ having one or two nonadjacent carbon atoms of the $C_{(1-12)}$ alkyl being replaced by an oxygen atom; and wherein:

$C^*$ is a chiral carbon atom;

n is four;

$R_4$ is a naturally occurring amino acid attached by an oxygen atom to the chiral carbon atom $C^*$ by an ester linkage, $-O-X(R_5)_m$; X being selected from the group consisting of C, P or S; m being two or three, depending on valence, and X being selected from the group consisting of C, P or S; wherein one $R_5$ is $=O$ and any other $R_5$ is a member independently selected from Group Q, and Group Q consists of:

hydroxyl group;

substituted or unsubstituted $C_{(3-10)}$ alkyl, $C_{(2-10)}$ alkenyl, $C_{(2-10)}$ alkynyl, $C_{(1-10)}$ alkoxyl, $C_{(1-10)}$ oxoalkyl, $C_{(1-10)}$ carboxyalkyl, $C_{(1-10)}$ hydroxyallyl, or substituted $C_{(1-2)}$ alkyl group;

$-OR_6$, $R_6$ being a substituted or unsubstituted $C_{(1-10)}$ alkenyl, $C_{(2-10)}$ alkynyl or $C_{(1-10)}$ oxoalkyl;

substituted or unsubstituted heterocylic group, attached to X through an atom within the ring, having one or two rings, each ring containing from four to seven atoms, wherein the heteroatom(s) of said heterocyclic group is 1 or 2 nitrogens; and substituted or unsubstituted carbocyclic group that is attached to X through a carbon atom within a ring, having one or two rings, each ring containing four to seven atoms, wherein the substituents of said substituted carbocyclic group are selected from the group consisting of amino, $C_{(2-6)}$ alkenyl, $C_{(1-6)}$ alkyl, $C_{(1-6)}$ alkoxyl, $C_{(1-6)}$ hydroxyakly, hydroxyl, $C_{(1-6)}$ oxoalkyl, azido, cyano, $C_{(2-6)}$ mono- or di-haloalkyl, isocyano, isothiocyano, imino, a chlorine atom, a bromine atom, a fluorine atom and an oxygen atom.

11. A pharmaceutical composition comprising a pharmaceutically acceptable excipient or carrier and a compound having the following structure:

12. The pharmaceutical composition of claim 11, wherein the pharmaceutical composition is formulated for oral administration.

13. The pharmaceutical composition of claim 11, wherein $R_5$ is trimethoxy-substituted phenyl.

14. The pharmaceutical composition of claim 11, wherein $R_4$ is glycinyl, isoleucinyl or valinyl.

15. A compound having the following structure:

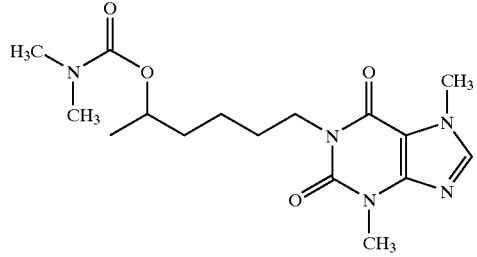

or a structure according to formula I:

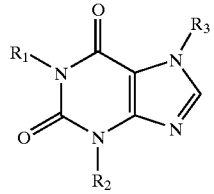

wherein $R_1$ or $R_2$ has the formula II:

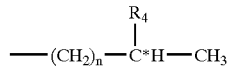

$R_1$ or $R_2$, which is other than formula II, and $R_3$ are independently $C_{(1-12)}$ alkyl, optionally, $R_2$ having one or two nonadjacent carbon atoms of the $C_{(1-12)}$ alkyl being replaced by an oxygen atom; and wherein:

C* is a chiral carbon atom;

n is four;

$R_4$ is a naturally occurring amino acid attached by an oxygen atom to the chiral carbon atom C* by an ester linkage, —O—X—$(R_5)_m$; being two or three, depending on valence, and X being selected from the group consisting of C, P or S; wherein one $R_5$ is =O and any other $R_5$ is a member independently selected from Group Q, and Group Q consists of:

hydroxyl group;

substituted or unsubstituted $C_{(3-10)}$ alkyl, $C_{(2-10)}$ alkenyl, $C_{(2-10)}$ alkynyl, $C_{(1-10)}$ alkoxyl, $C_{(1-10)}$ oxoalkyl, $C_{(1-10)}$ carboxyalkyl, $C_{(1-10)}$ hydroxyalkyl, or substituted $C_{(1-2)}$ alkyl group;

—OR, $R_6$ being a substituted or unsubstituted $C_{(1-10)}$ alkyl, $C_{(2-10)}$ alkenyl, $C_{(2-10)}$ alkynyl, or $C_{(1-10)}$ oxoalkyl;

substituted or unsubstituted heterocylic group, attached to X through an atom within the ring, having one or two rings, each ring containing from four to seven atoms, wherein the heteroatom(s) of said heterocyclic group is 1 or 2 nitrogens; and substituted or unsubstituted carbocyclic group that is attached to X through a carbon atom within a ring, having one or two rings, each ring containing four to seven atoms, wherein the substituents of said substituted carbocyclic group are selected from the group consisting of amino, $C_{(2-6)}$ alkenyl, $C_{(1-6)}$ alkyl, $C_{(1-6)}$ alkoxyl, $C_{(1-60)}$ hydroxyalkyl, hydroxyl, $C_{(1-6)}$ oxoalkyl, azido, cyano, $C_{(2-6)}$ mono–or di–haloalkyl, isocyano, isothiocyano, imino, a chlorine atom, a bromine atom, a fluorine atom and an oxygen atom.

16. A compound according to claim 1, wherein $R_2$ and $R_3$ are methyl, and wherein $R_6$ is a substituted or unsubstituted $C_{(1-10)}$ alkyl, $C_{(2-10)}$ alkenyl, $C_{(2-10)}$ alkynyl, or $C_{(1-10)}$ oxoalkyl;

substituted or unsubstituted heterocylic group, attached to X through an atom within the ring, having one or two rings, each ring containing from four to seven atoms, and a single nitrogen as the heteroatom; or substituted or unsubstituted carbocyclic group that is attached to X through a carbon atom within a ring, having one ring containing four to seven atoms, wherein the substituents of said substituted carbocyclic group are selected from the group consisting of amino, $C_{(2-6)}$ alkenyl, $C_{(1-6)}$ alkyl, $C_{(1-6)}$ alkoxyl, $C_{(1-6)}$ hydroxyalkyl, hydroxyl, $C_{(1-6)}$ oxoakyl, azido, cyano, $C_{(2-6)}$ mono- or di-haloalkyl, isocyano, isothiocyano, imino, a chlorine atom, a bromine atom, a fluorine atom and an oxygen atom.

17. A compound according to claim 1, wherein $R_3$ is methyl.

18. A compound according to claim 17, wherein $R_2$ is methyl.

19. A compound according to claim 18, wherein X is S.

20. A compound according to claim 19, wherein members of Group Q are independently selected from the group consisting of an hydroxyl group, substituted or unsubstituted $C_{(3-10)}$ alkyl, $C_{(2-10)}$ alkenyl, $C_{(2-10)}$ alkynyl, $C_{(1-10)}$ alkoxyl, $C_{(1-10)}$ oxoalkyl, $C_{(1-10)}$ carboxyalkyl, $C_{(1-10)}$ hydroxyalkyl; and a substituted $C_{(1-2)}$ alkyl group.

21. A compound according to claim 20, wherein the other $R_5$ is OH.

* * * * *